US012773445B2

(12) United States Patent
Odunsi et al.

(10) Patent No.: US 12,773,445 B2
(45) Date of Patent: Oct. 27, 2026

(54) MAJOR HISTOCOMPATIBILITY COMPLEX CLASS II-EXPRESSING CANCER CELL VACCINE AND METHODS OF USE FOR PRODUCING INTEGRATED IMMUNE RESPONSES

(71) Applicant: Health Research, Inc., Buffalo, NY (US)

(72) Inventors: Kunle Odunsi, Williamsville, NY (US); Takemasa Tsuji, Williamsville, NY (US); Junko Matsuzaki, Williamsville, NY (US)

(73) Assignee: Health Research, Inc., Buffalo, NY (US)

( * ) Notice: Subject to any disclaimer, the term of this patent is extended or adjusted under 35 U.S.C. 154(b) by 1089 days.

(21) Appl. No.: 17/262,163

(22) PCT Filed: Jul. 22, 2019

(86) PCT No.: PCT/US2019/042764
§ 371 (c)(1),
(2) Date: Jan. 21, 2021

(87) PCT Pub. No.: WO2020/023350
PCT Pub. Date: Jan. 30, 2020

(65) Prior Publication Data

US 2021/0268087 A1 Sep. 2, 2021

Related U.S. Application Data

(60) Provisional application No. 62/701,791, filed on Jul. 22, 2018.

(51) Int. Cl.

| | |
|---|---|
| ***A61K 39/00*** | (2006.01) |
| ***A61P 35/00*** | (2006.01) |
| ***C07K 14/705*** | (2006.01) |
| ***C12N 15/85*** | (2006.01) |
| *C12N 5/09* | (2010.01) |

(52) U.S. Cl.
CPC .......... *A61K 39/0011* (2013.01); *A61P 35/00* (2018.01); *C07K 14/70575* (2013.01); *C12N 15/85* (2013.01); *A61K 2039/5152* (2013.01); *A61K 2039/575* (2013.01); *C12N 5/0693* (2013.01); *C12N 2510/00* (2013.01)

(58) Field of Classification Search
CPC ........ A61K 39/0011; A61K 2039/5152; A61K 2039/575; A61K 35/12; A61P 35/00; C12N 15/85; C12N 2510/00; C12N 5/0693; C07K 14/4702; C07K 14/70575
See application file for complete search history.

(56) References Cited

U.S. PATENT DOCUMENTS

| | | | |
|---|---|---|---|
| 6,514,685 | B1 | 2/2003 | Moro |
| 2009/0047262 | A1 | 2/2009 | Drozina et al. |
| 2010/0240585 | A1 | 9/2010 | Shirwan et al. |
| 2013/0209514 | A1 | 8/2013 | Gilboa et al. |

FOREIGN PATENT DOCUMENTS

| | | | | |
|---|---|---|---|---|
| EP | 1060247 | B1 | 12/2000 | |
| WO | WO-9426290 | A1 * | 11/1994 | ............. C07K 14/52 |
| WO | 99/42585 | A1 | 8/1999 | |
| WO | 2010/121180 | A1 | 10/2010 | |
| WO | 2011/097477 | A1 | 8/2011 | |
| WO | WO-2016037009 | A1 * | 3/2016 | ....... G01N 33/57415 |
| WO | 2017173321 | A1 | 10/2017 | |
| WO | 2018026911 | A1 | 2/2018 | |

OTHER PUBLICATIONS

Tian et al. (Signal Transduct. Target. Ther. Nov. 18, 2016: 1: 16025; pp. 1-10).*
Accolla et al. (Front. Immunol. Jul. 30, 2019: 10: 1806; pp. 1-8).*
Bitra et al. (J. Biol. Chem. Feb. 8, 2019; 294 (6): 1831-45).*
Regal et al. (Am. J. Physiol. Heart Circ. Physiol. 2020; 318: H726-H728).*
Mortara et al. (Clin. Cancer Res. Jun. 1, 2006; 12 (11 Pt 1): 3435-43).*
Mortara et al. (Surg Oncol. Dec. 2007; 16 (Suppl 1): S33-6).*
Ostrand-Rosenberg (Grant No. DAMD17-94-J-4323; Sep. 13, 1995; pp. 1-12).*
Yurkovetsky et al. (J. Gene Med. Feb. 2006; 8 (2): 129-37).*
Mortara et al. (Int. Immunol. Jun. 2009; 21 (6): 655-65).*
Meazza et al. (Eur. J. Immunol. May 2003; 33 (5): 1183-92).*
Li et al. (Cell. Mol. Immunol. Oct. 2008; 5 (5): 379-84).*
Eddine et al. (Oncoimmunology. Nov. 28, 2016; 6 (1): e1261777; pp. 1-11).*
Vinay et al. (Mol. Cancer Ther. May 2012; 11 (5): 1062-70).*
Tugues et al. (Cell Death Differ. Feb. 2015; 22 (2): 237-46).*
Machado et al. (Int. J. Mol. Sci. Feb. 2021; 22 (3): 1074; pp. 1-19).*
Eckstrum et al. (Cell Tissue Res. Jun. 2011; 344 (3): 567-76; author manuscript; pp. 1-15).*
Battin et al. (Cancer Immunol. Immunother. Sep. 2023; 72 (9): 3029-43).*

(Continued)

*Primary Examiner* — Hong Sang
(74) *Attorney, Agent, or Firm* — Hodgson Russ LLP

(57) ABSTRACT

Provided are modified cancer cells that are modified to co-express class II trans-activator (CIITA), and an immuno-stimulatory molecule. The immuno-stimulatory molecule is OX-40-ligand or 4-IBB-Ligand. Methods of making the cells are provided by introducing polynucleotides encoding the CIITA and the immune-stimulatory molecule into cancer cells. Methods of stimulating humoral and cell-mediated immune responses by administering the modified cancer cells, or polynucleotides encoding the CIITA and immune-stimulatory molecules are also provided. These approaches can be used to stimulate an immune response against any of a wide variety of cancer antigens.

5 Claims, 8 Drawing Sheets

Specification includes a Sequence Listing.

(56) References Cited

OTHER PUBLICATIONS

Bitra et al. (Int. J. Mol. Sci. Feb. 2021; 22 (3): 1074; pp. 1-19).*
Bitra et al. (J. Biol. Chem. Jun. 29, 2018; 293 (26): 9958-69).*
Bitra et al. (FASEB J. 2019; 33 (Suppl. 1): 461.3; pp. 1-3).*
"4-1BB agonists: multi-potent potentiators of tumor immunity," Bartkowiak et al, Front. Oncol. Sec. Cancer Immunity and Immunotherapy, vol. 5 (Year: 2015).*
"Irradiated CIITA-positive mammary adenocarcinoma cells act as a potent anti-tumor-preventative vaccine by inducing tumor-specific CD4+ T cell priming and CD8+ T cell effector functions," Mortara et al, International Immunology, vol. 21, No. 6, pp. 655-665 (Year: 2009).*
"Induction of Immunity to neuroblastoma early after syngeneic Hematopoietic Stem Cell Transplantation Using a Novel Mouse Tumor Vaccine," Jing et al, Biology of Blood and Marrow Transplantation, vol. 13, Issue 3, pp. 277-292 (Year: 2007).*
"Follicular lymphoma and the immune system: from pathogenesis to antibody therapy," Stevenson et al, Blood, vol. 119, No. 16 (Year: 2012).*
"MHC Class II as a therapeutic target in B-cell lymphomas: the CIITA road to paradise?" Diepstra et al, Leukemia and Lymphoma, 50:11, 1740-1741 (Year: 2009).*
"Turning T cells on: epigenetically enhanced expression of effector T-cell costimulatory molecules on irradiated human tumor cells," Journal for Immuno Therapy of Cancer, 1:17 (Year: 2013).*
"Tumor Specific Immunotherapy of Mammary Cancer," Ostrand-Rosenberg (Year: 1995).*
Jing, W., et al., Induction of Immunity to Neuroblastoma Early after Syngeneic Hematopoietic Stem Cell Transplantation Using a Novel Mouse Tumor Vaccine, Biology of Blood and Marrow Transplantation, Mar. 2007, vol. 13, No. 2, pp. 277-292.
Chou, S.D., et al., Histone acetylation regulates the cell type specific CIITA promotors, MHC class II expression and antigen presentation in tumor cells, International Immunology, Oct. 6, 2005, vol. 17, No. 11, pp. 1483-1494.
Lu, Z.Y., et al., B7-1 and 4-1BB ligand expression on a myeloma cell line makes it possible to expand autologous tumor-specific cytotoxic T cells in vitro, Experimental Hematology, Aug. 21, 2007, vol. 35, No. 3, pp. 443-453.
De Charette, M., et al., Turning tumour cells into antigen presenting cells: The next step to improve cancer immunotherapy?, European Journal of Cancer, Nov. 2016, vol. 68, pp. 134-147.
Wang, Y., et al., Curative Antitumor Immune Response Is Optimal with Tumor Irradiation Followed by Genetic Induction of Major Histocompatibility Complex Class I and Class II Molecules and Suppression of Ii Protein, Human Gene Therapy, Mar. 10, 2005, vol. 16, Issue 2, pp. 187-199.

* cited by examiner

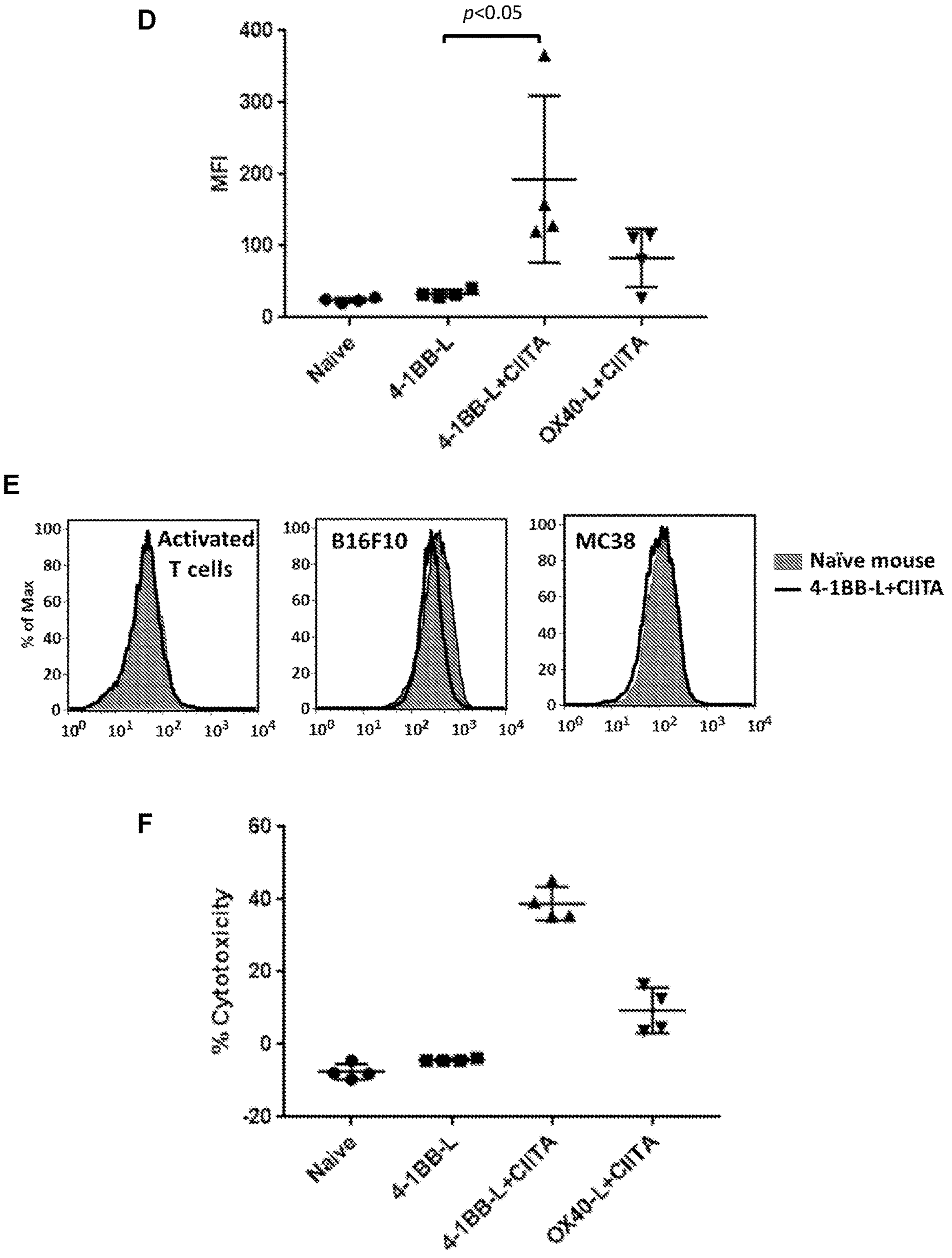
Figure 4, continued

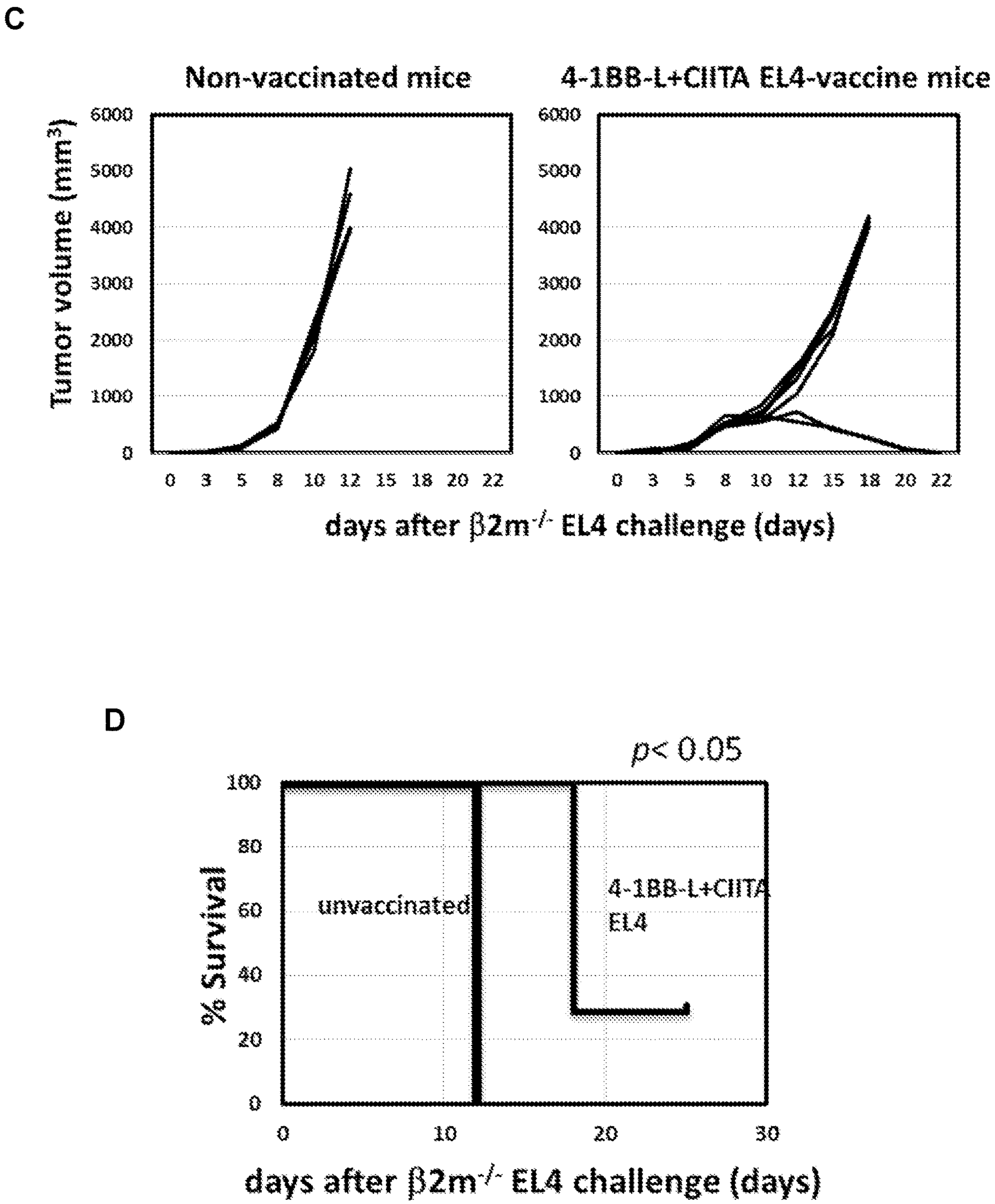
Figure 5, continued

MAJOR HISTOCOMPATIBILITY COMPLEX CLASS II-EXPRESSING CANCER CELL VACCINE AND METHODS OF USE FOR PRODUCING INTEGRATED IMMUNE RESPONSES

CROSS-REFERENCE TO RELATED APPLICATIONS

This application claims priority to U.S. provisional application No. 62/701,791, filed Jul. 22, 2018, the disclosure of which is incorporated herein by reference.

FIELD

The present disclosure relates generally to prophylaxis and therapy of cancer, and more specifically to compositions and methods for improving immune responses to cancer.

BACKGROUND

Tumor antigen-specific CD4+ T cells, CD8+ T cells and B cells play cooperative roles in antitumor immunity. At the tumor site, CD8+ T cells, also known as cytotoxic T cells, are considered to be the main effector cells to destroy cancer cells. CD4+ T cells, also known as helper T cells, help the activation, function and maintenance of CD8+ T cells through activation of antigen-presenting cells and/or secreting cytokines. CD4+ T cells also help activation of B cells to induce antibody secretion by expressing CD40-ligand (CD40L) which binds to CD40 molecule on B cells, and secreting cytokines that induce antibody class-switching. B cells produce tumor antigen-specific antibodies that bind to tumor antigen proteins to form antigen-antibody complex, sometimes referred to as an "immune complex". Immune complexes are efficiently captured by antigen-presenting cells and at the same time activate antigen-presenting cells (APCs) through binding to Fc receptors. Subsequently, activated antigen-presenting cells cross-present tumor antigen proteins to CD4+ and CD8+ T cells. Because of the distinct and collaborative antitumor functions by CD4+ T cells, CD8+ T cells and B cells, a strategy which would establish integrated CD4+ T cells, CD8+ T cells and antibody-secreting B cells would be a promising immunotherapy for cancer patients.

T cells destroy cancer cells by recognizing tumor antigen protein-derived peptides presented on MHC molecules on cancer cells. However, it is known that some cancer cells escape from T cell-mediated killing by eliminating MHC molecules from their surface. Antibodies that bind on cell surface of cancer cells destroy cancer cells through antibody-dependent cellular cytotoxicity (ADCC) and complement-dependent cytotoxicity (CDC) irrespective of MHC expression (or in a MHC-independent manner).

CD4+ helper T cells are considered to play a central role in inducing integrated antitumor immune response, because they help both CD8+ T cells and B cells. Generally, activation of CD4+ T cells requires antigen-presenting cells that capture and cross-present extracellular proteins such as tumor antigen proteins. Recently, we have discovered a unique CD4+ T-cell subset which directly recognizes MHC class II (MHC-II)-expressing cancer cells. This CD4+ T-cell subset, which we named "tumor-recognizing CD4+ T cells (TR-CD4 cells)", enhanced function of tumor antigen-specific CD8+ T cells by directly recognizing cancer cells without the need for antigen-presenting cells. Therefore, TR-CD4 cells are expected to efficiently provide help to other immune cells to enhance antitumor immunity at the tumor site. However, there is no presently known method to efficiently induce TR-CD4 cells in the body. Thus, there is an oncoming and unmet need for compositions and methods to improve immune responses to cancer, and other immunogenic agents. The present disclosure is related to these needs.

BRIEF SUMMARY

The present disclosure provides compositions and methods that are useful for stimulating and/or enhancing immune responses, including but not necessarily limited to immune responses to peptide antigens. In embodiments, cell-mediated immunity, humoral immunity, or both are stimulated and/or enhanced by using the compositions and methods of this disclosure.

The disclosure in certain aspects comprises compositions for use in vaccination. In embodiments, the disclosure provides cellular vaccine compositions comprising modified cancer cells that are engineered to overexpress class II trans-activator (CIITA) gene, and an immuno-stimulatory molecule. The immuno-stimulatory molecules described in this disclosure include GM-CSF, CD80, GITR-Ligand, OX-40-ligand, and 4-1BB-Ligand. In one embodiment, CD86 may be used. In embodiments, modified cancer cells express 4-BB-ligand and/or OX40-ligand, as described further below. In alternative embodiments, the disclosure includes using polynucleotides that encode the CIITA protein, and the immune-stimulatory agents, such as in expression vectors, as the agents that are delivered to an individual. In embodiments, as an alternative to the CIITA gene, the disclosure includes engineering cancer cells to increase expression of MHC II alpha and beta chains.

Using relevant mouse models, vaccines described herein are demonstrated to induce potent and long-lasting antitumor CD8+ T cells, compared to cancer cells expressing CIITA or the co-stimulatory ligand alone. Further, cellular vaccines described herein induce production of cytotoxic antibodies against cell surface molecules on cancer cells. Therefore, the vaccines described herein are expected to provide protective immunity against MHC-expressing cancers by T cell-mediated cytotoxicity, but also MHC-loss immune escape variants, by antibody-mediated cytotoxicity.

It will be recognized by those skilled in the art that the term MHC as used herein is extendable to human applications via the MHC human equivalent, referred to in the art as leukocyte antigen gene complex (HLA).

As will be recognized by the non-limiting examples presented with this disclosure, in order to induce TR-CD4 cells, we expressed MHC-II on cell surface of murine cancer cell lines by retrovirally overexpressing MHC class II trans-activator (CIITA) gene, which is a master regulator of MHC class II-mediated antigen presentation. To enhance immunogenicity of MHC-II-expressing cancer cells, an immuno-stimulatory gene was also co-overexpressed. In contrast to the parental cancer cells or cells that expressing CIITA-alone, some engineered cancer cell lines co-expressing CIITA and an immuno-stimulatory gene, particularly 4-1BB-ligand (BB-L), induced strong and long-lasting antitumor immune response in syngeneic mice. Cancer cells that co-express CIITA+BB-L, but which do not express BB-L alone, induced circulating antibodies that specifically bind on surface of cancer cells and kill cancer cells. Cancer-specific antibodies induced by CIITA+BB-L-expressing cancer cells protected mice against MHC-loss cancer cell growth. These findings show that engineered cancer cells that co-express CIITA+BB-L are suitable for use as vaccines to induce integrated T-cell and antibody response for protection against MHC-expressing and MHC-loss cancers.

DETAILED DESCRIPTION

Figure 1:
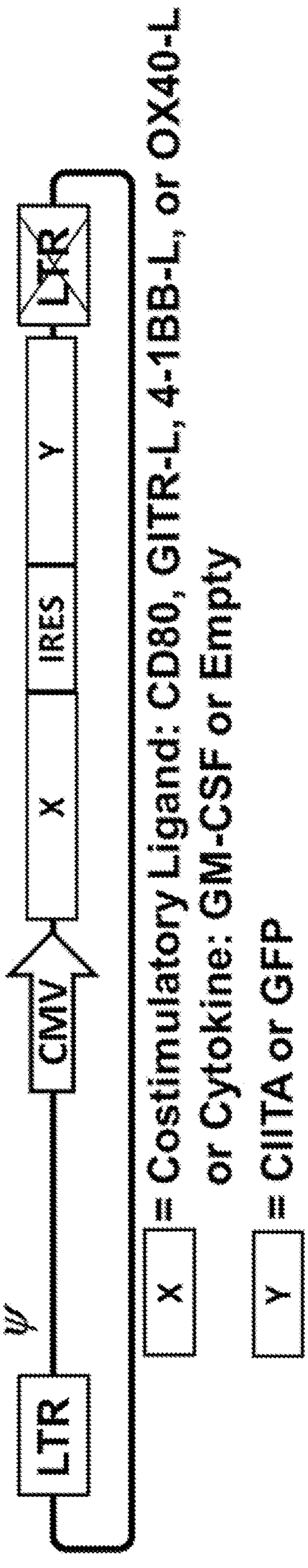
FIG. 1. Generation of murine cancer cell lines co-expressing CIITA and immuno-stimulatory genes. CIITA and/or immunostimulatory gene (CD80, GM-CSF, GITR-Ligand, 4-1BB-Ligand, and OX40-Ligand) were cloned into a bicistronic retroviral transfer plasmid (pQCXIX, purchased from Clontech). Retroviral particles were produced by co-transfection of GP2-293 packaging cell line (Clontech) of the transfer plasmid and the pVSV-G envelope-expressing plasmid (Clontech). Murine cancer cell lines were engineered to express CIITA and/or an immuno-stimulatory gene by retroviral transduction.

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof, and includes all compositions of matter including but not necessarily limited to vectors, cloning intermediates, cells, cell cultures, progeny of the cells, and the like.

The disclosure includes but is not limited to engineered immunogenic cancer cells described herein, cancer vaccines made using the immunogenic cancer cells, methods of making the immunogenic cancer cells, immunogenic compositions, polynucleotides, and methods for the treatment of cancer. The disclosure includes all polynucleotides disclosed herein, their complementary sequences, and reverse complementary sequences. For any reference to a polynucleotide or amino acid sequence by way of a database entry, the polynucleotide and amino acid sequence presented in the database entry is incorporated herein as it exists on the effective filing date of this application or patent.

As discussed above, cancer cells express an array of immunogenic antigens that are recognized by T cells and B cells. Therefore, the present disclosure utilizes modified cancer cells as potent vaccines to induce polyvalent immune response.

In embodiments, the disclosure comprises modifying cancer cells as described herein, and comprises the modified cancer cells themselves, and compositions, such as pharmaceutical compositions, comprising the cancer cells. In embodiments, the cancer cells are of any cancer type, including solid and liquid tumors. In embodiments, cancer cells modified according to this disclosure include but are not necessarily limited to breast cancer, prostate cancer, pancreatic cancer, lung cancer, liver cancer, ovarian cancer, cervical cancer, colon cancer, esophageal cancer, stomach cancer, bladder cancer, brain cancer, testicular cancer, head and neck cancer, melanoma, skin cancer, any sarcoma, including but not limited to fibrosarcoma, angiosarcoma, adenocarcinoma, and rhabdomyosarcoma, and any blood cancer, including all types of leukemia, lymphoma, or myeloma.

In embodiments, a cellular vaccine composition described herein is administered to an individual who has cancer, or previously had cancer, or is at risk for developing cancer. The cancer can be any of the aforementioned types. In embodiments, modified cancer cells for use as vaccines of this disclosure comprise cancer cells from a cancer cell line. In embodiments, modified cancer cells for use as vaccines of this disclosure comprise cancer cells from an individual, and are modified such that they express or overexpress CIITA and one or more co-stimulatory molecules or immunostimulatory cytokines, as described herein, and are provided to the same individual as a cancer therapy. In embodiments, allogenic cancer cells are modified and used in the methods described herein. In embodiments, the modified cancer cells are the same cancer type as a cancer against which a therapeutic immune response is generated in an individual.

In embodiments, the individual may be vaccinated with one or more antigens that are expressed by the modified cancer cells (or the cancer cells that are targeted using polynucleotides, as described herein). In embodiments, a tumor or cancer cell lysate may be used as the vaccination.

In embodiments, immunological protection elicited by methods of the present disclosure (with or without subsequent vaccination) can be durable, and last for days, weeks or months, or longer, including but not limited to after vaccination, and such vaccinations can be effective to elicit protection after a single dose, or multiple doses. Booster vaccinations can be used according to schedules that are known in the art and can be adapted for use with methods of this disclosure when provided the benefit of this specification, and include such approaches as a Prime-Boost strategy.

With respect to immune responses that are stimulated and/or enhanced as described herein, for induction of TR-CD4 cells by cancer cell-based vaccines, cancer cells need to express MHC-II (or HLA, in the case of humans). However, not all cancer cells constitutively express cell surface MHC-II. For instance, none of murine cancer cell lines, including but not necessarily limited to EL4 lymphoma, B16F10 melanoma, MC38 colon cancer, and ID8 ovarian cancers, express constitutive MHC-II.

In order to express MHC-II on cell surfaces of murine cancer cell lines, we retrovirally overexpressed MHC class II transactivator (CIITA) gene, which is a master regulator of MHC class II-mediated antigen presentation. Thus, in embodiments, each cancer cell modified for use as a vaccine as described herein will either be modified such that it expresses CIITA if it did not previously express it, or will be modified such that it expresses more CIITA, relative to the amount expressed prior to being modified according to this disclosure. Those skilled in the art will recognize that CIITA is also referred to as C2TA, NLRA, MHC2TA, and CIITAIV.

Instead of using the CIITA gene, overexpression of MHC class II alpha and beta chain genes are expected to induce cell surface MHC class II expression. Thus, in embodiments, engineering of cancer cells using recombinant molecular biology approaches, such as by direction introduction of MHC alpha and beta chain encoding polynucleotides, is considered to be an alternative approach to provide modified cancer cell vaccines that will function in a manner similar to cancer cells modified as otherwise described herein. In certain embodiments, the disclosure provides for increasing MHC or HLA expression by introducing polynucleotides directly, or to produce modified cancer cells, using polynucleotides that encode HLA class II alpha and beta chains. HLA class II alpha and beta chains for any particular individual can be determined using techniques that are well established in the art. In embodiments, preexisting cancer cells that are matched to an individual's HLA type can be used. Alternatively, any biological sample from an individual that comprises nucleated cells can be tested to determine the HLA type of the individual, and suitable polynucleotides encoding the pertinent HLA class II alpha and beta chains can be designed and produced, and used in embodiments of this disclosure. In embodiments, the HLA class II alpha chains are for HLA-DM, HLA-DMA, HLA-DO, HLA-DOA, HLA-DP, HLA-DPA1, HLA-DQ, HLA-DQA1, HLA-DQA2, HLA-DR or HLA-DRA, or any subtype of these HLA types. In embodiments, the HLA class II beta chains are for HLA-DMB, HLA-DOB, HLA-DPB1, HLA-DQB1, HLA-DQB2, HLA-DRB1, HLA-DRB3, HLA-DRB4, or HLA-DRB5, or any subtype of these HLA types.

Representative and non-limiting examples of murine and human amino acid sequences of CIITA, and co-expressed proteins, as well as DNA sequences encoding them, are provided below. The disclosure includes using nucleotide and amino acid sequences that are different from those provided here, so long as the modified cancer cells function to enhance immune responses relative to unmodified cancer cells. In embodiments, the cancer cells express CIITA and co-stimulatory molecules or immuno-stimulatory cytokines described herein that are identical to the amino acid sequences described below, or have at from 70-99% amino acid identity with the pertinent sequences. The disclosure includes using proteins with amino acid insertions, deletions, and substitutions, provided they retain their intended function. All polynucleotide sequences encoding the proteins described herein are encompassed by this disclosure, and are not to be limited by those presented below.

Examples of this disclosure combine engineered expression or overexpression of CIITA with one or a combination of G-CSF, CD80, GITR-Ligand, OX-40-ligand, and 4-1BB-Ligand. However, it is demonstrated that co-expression of CIITA with 4-1BB-L is superior to the other co-expressed proteins. Thus, in embodiments, the disclosure provides compositions and methods for use as cancer vaccines that comprise modified cancer cells that are engineered by recombinant molecular biology approaches to express CIITA and an immuno-stimulatory that is preferably 4-1BB-L, although the other immuno-stimulatory factors are included within the scope of this disclosure.

In embodiments, use of a cellular cancer vaccine described herein comprises a cancer therapy. In embodiments, use of a cellular cancer vaccine described herein produces a durable memory response, including but not necessarily limited to a durable CD8+ T cell memory response. In embodiments, a single administration of a cellular vaccine composition described herein produced an immune response that lasts at least from at least one month, to at least one year, or for at least one year, or will provide life-long protection, and thus for use in humans or non-human animals can last for decades. Thus, human and veterinary uses are included.

In embodiments, use of a cellular cancer vaccine or related polynucleotide as described herein produces any one or any combination of results, which can be compared to any suitable reference: improved activation of T cells, increase of TR-CD4+ T cells, improved CD8+ memory cell production and/or persistence, improved production of anti-cancer antibodies, improved inhibition of tumor growth, and improved survival time. In embodiments, a vaccination of this disclosure prevents formation of tumors, or limits growth of an existing tumor, or eradicates existing tumors. In embodiments, the reference is obtained by cancer cells that express a different immune-stimulatory molecule than the immune-stimulatory molecule that was a component of an improved immune response. In embodiments, the ability of a vaccine described herein to improve response to rechallenge with cancer cells is improved.

Vectors encoding the CIITA and or the co-stimulatory molecules can be any suitable vector or other polynucleotide. One or more vectors or polynucleotides can be used. In non-limiting embodiments, retroviral vectors may be used. FIG. 1 provides a non-limiting embodiment of a suitable vector. In embodiments, a sequence encoding, or designed to encode CIITA once integrated, is used alone in a vector. In embodiments, a sequence encoding, or designed to encode a co-stimulatory molecule once integrated is used alone in a vector. In embodiments, a single vector encodes or is designed to encode both the CIITA and co-stimulatory molecule. Thus, in embodiments, the disclosure comprises polycistronic vectors. In embodiments, the CIITA and the sequence encoding the co-stimulatory molecule are separated by, for example, and internal ribosome entry sequence (IRES).

In embodiments, the cancer cell vaccines, or polynucleotides encoding the proteins described herein, are used concurrently or sequentially with conventional chemotherapy, or radiotherapy, or another immunotherapy, or before or after a surgical intervention, such as a tumor resection. In embodiments, the cancer cell vaccines, or polynucleotides encoding the proteins that are recombinantly expressed by the cancer cell vaccines, are used in single, or multiple doses. In embodiments, the cancer vaccines are provided only once, or weekly, monthly, every 3 months, every 6 months, yearly, or in a pre-determined interval of years.

Cancer cell vaccines described herein can be administered to an individual in need thereof using any suitable route, including parenteral, subcutaneous, intraperitoneal, intrapulmonary, and intranasal. Parenteral infusions include intramuscular, intravenous, intraarterial, intraperitoneal, or subcutaneous administration. In embodiments, an amount of cancer cells administered comprises an effective dose. In embodiments, an effective dose comprises sufficient cells to produce one or more effects described herein, including any cell-mediated response, or humoral response, or a combination thereof, which is effective to inhibit growth of cancer, and/or generate an anti-cancer memory response. In embodiments, $10^4$ to $10^9$ modified cancer cells are introduced. In embodiments, a cancer cell composition of this disclosure for use as a vaccine comprises isolated cells modified as described herein, wherein all or some of the cancer cells are modified. In embodiments, the disclosure includes compositions comprising cells, wherein from 1-100% of the cells are modified cancer cells. In embodiments, the disclosure provides compositions comprising cancer cells, wherein 1-100% of the cancer cells are modified cancer cells. Those skilled in the art will recognize that retention of cancer cell morphology is a solution is pertinent to the modified cancer cell phenotype. In embodiments, modified cancer cells can be included in a pharmaceutical composition. Modified cancer cells and/or polynucleotides of the present disclosure can be provided in pharmaceutical compositions by combining them with any suitable pharmaceutically acceptable carriers, excipients and/or stabilizers. Examples of pharmaceutically acceptable carriers, excipients and stabilizer can be found in Remington: The Science and Practice of Pharmacy (2005) 21st Edition, Philadelphia, PA. Lippincott Williams & Wilkins, the disclosure of which is incorporated herein by reference.

In embodiments, one or more recombinant polynucleotide described herein for use in making the cellular vaccine formulations, or another therapeutic polynucleotide, can be used as the agent that is delivered to the individual, and thus the polynucleotides themselves may comprise a therapeutic agent. In embodiments, a composition delivered to an individual according to this disclosure can be a cell-free composition. In embodiments, a combination of modified cancer cells, and polynucleotides that are not in cells, can be used.

In embodiments, if a therapeutic agent used in a method of this disclosure is a polynucleotide, it can be administered to the individual as a naked polynucleotide, in combination with a delivery reagent, or as a recombinant plasmid or viral vector which comprises and/or expresses the polynucleotide agent. In one embodiment, the proteins are encoded by a recombinant oncolytic virus, which can specifically target cancer cells, and which may be non-infective to non-cancer cells, and/or are eliminated from non-cancer cells if the oncolytic virus enters the non-cancer cells. Examples of recombinant oncolytic viruses that can be used with this disclosure include but are not limited to recombinant vaccinia virus (rOVV). In embodiments, one or more polynucleotides described herein can be delivered via a modified virus comprising a modified viral capsid or other protein that is targeted to, and thus will bind with specificity, to one or more ligands that are preferentially or exclusively expressed by cancer cells. In embodiments, separate polynucleotides encoding distinct proteins described herein can be used. In embodiments, one or more polynucleotides described herein can be injected directly into a tumor.

Polynucleotide therapeutic agents of this disclosure can be combined if desired with a delivery agent. Suitable delivery reagents for administration include but are not limited to Mirus Transit TKO lipophilic reagent; lipofectin; lipofectamine; cellfectin; or polycations (e.g., polylysine), liposomes, or combinations thereof.

Therapy or inhibition of cancer as described herein may be combined with any other anti-cancer approach, such as surgical interventions and conventional chemotherapeutic agents. In embodiments, cancer treatment according to this disclosure can be combined with administration of one or more immune checkpoint inhibitors. In embodiments, the checkpoint inhibitors comprise an anti-programmed cell death protein 1 (anti-PD-1) checkpoint inhibitor, or an anti-Cytotoxic T-lymphocyte-associated protein 4 (anti-CTLA-4) checkpoint inhibitor. There are numerous such checkpoint inhibitors known in the art. For example, anti-PD-1 agents include Pembrolizumab and Nivolumab. An anti-PD-L1 example is Avelumab. An anti-CTLA-4 example is Ipilimumab.

In certain non-limiting demonstrations in the examples below, immunogenicity of engineered cancer cells is analyzed using syngeneic C57BL/6 mice in with modified lymphoma, colon cancer cells, melanoma and ovarian cancer cell lines, all of which demonstrate co-expression of CIITA and 4-1BB-L is an effective approach to stimulating potent anticancer responses. Thus, and without intending to be bound by any particular theory, it is expected that the approaches described herein, and particularly co-expression of CIITA with 4-1BB-L, will be broadly applicable to a wide variety of cancer types, and will function with the same or similar efficacy in humans, given that clinically relevant mouse models are used to demonstrate aspects of the disclosure.

Aspects of the disclosure are demonstrated by the following examples, which are intended to illustrate but not limit the disclosure.

EXAMPLES

Immunogenicity of the engineered cancer cells was investigated by introducing them into syngeneic C57BL/6 mice.

Figure 2:
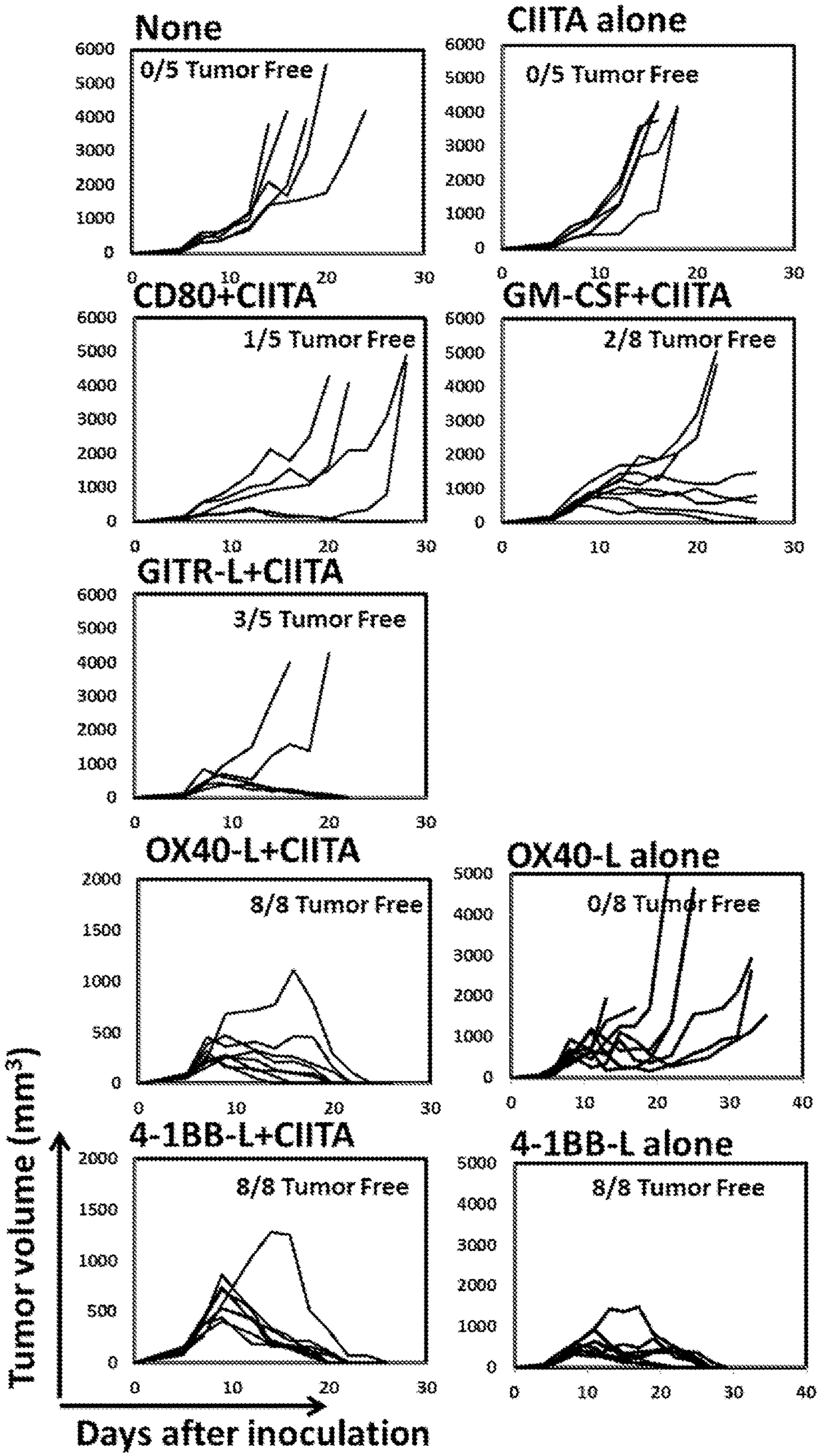
FIG. 2. Immunogenicity of engineered cancer cells. Effect of expression of CIITA and an immuno-stimulatory genes on growth of a murine lymphoma cell line, EL4, in syngeneic (C57BL/6) mice. Mice were subcutaneously injected with EL4 cells that were engineered to express indicated gene(s). Tumor volume was calculated from diameters as 0.5×(shorter diameter)$^2$×(longer diameter). Expression of CIITA alone did not alter tumor growth of EL4. Co-expression of CIITA and an immune stimulatory gene significantly delayed tumor growth. In particular 4-1BB-L and OX40-L induced spontaneous complete regression in all mice. Whereas expression of 4-1BB-L alone induced complete regression, OX-40L alone only partially delayed tumor growth.

In an EL4 lymphoma model, overexpression of CIITA alone did not change tumor growth as compared to the parental EL4. In contrast, co-expression of CIITA and immuno-stimulatory molecules significantly delayed tumor growth. In particular, EL4 co-expressing OX40-L+CIITA or 4-1BB-L+CIITA was completely rejected. In this model, 3 groups that received EL4 overexpressing OX40-L+CIITA, 4-1BB-L+CIITA, and 4-1BB-L alone showed complete tumor elimination in all mice (FIG. 2).

Figure 3:
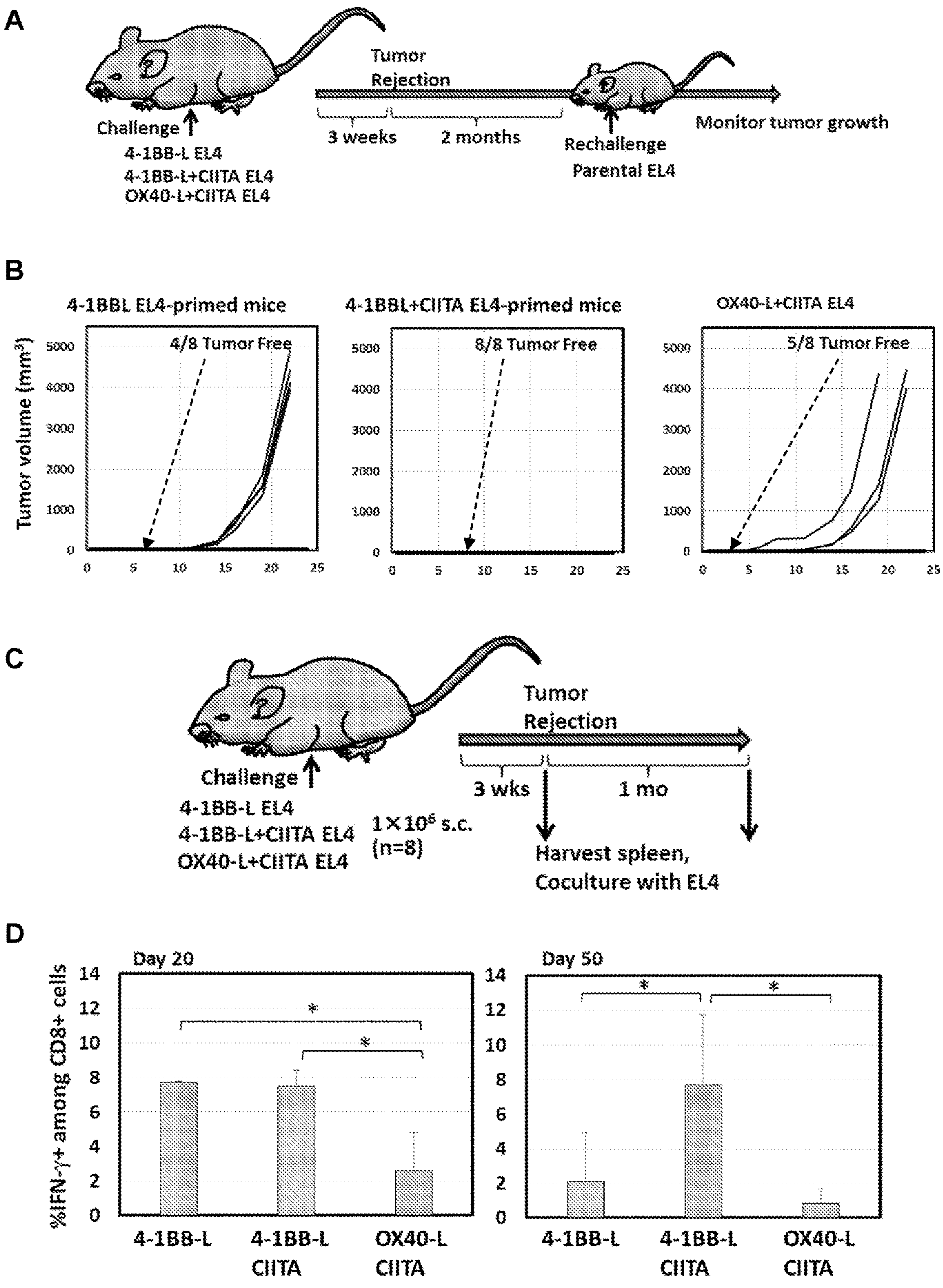
FIG. 3. Induction of memory CD8+ T-cell response by engineered cancer cells. (A) Experimental approach. To investigate long-term antitumor memory immune response, mice were first inoculated with EL4 engineered with 4-1BB-L alone, CIITA+4-1BB-L, or CIITA+OX40-L. Two months after complete regression, mice were subcutaneously re-challenged with the parental EL4 and tumor growth was monitored. (B) Growth of the parental EL4 after rechallenge. Only some mice that rejected EL4 expressing 4-1BB-L alone or CIITA+OX40-L showed protection upon rechallenge. In contrast, all mice that initially received EL4-expressing CIITA+4-1BB-L rejected rechallenged parental EL4. (C) To investigate memory CD8+ T-cell responses, mice were first inoculated with the indicated engineered EL4. Immediately and one month after complete regression, EL4-specific CD8+ T cells in the spleen were investigated by coculture with the parental EL4 and measure cytokine production by intracellular cytokine staining assay. (D) Immediately after tumor regression (Day 20), mice that received EL4 expressing 4-1BB-L alone and CIITA+4-1BB-L showed similar EL4-specific CD8+ T cells. Mice that received CIITA+OX40-L showed decreased EL4-specific CD8+ T cells. One month after (Day 50), whereas mice that received EL4 expressing 4-1BB-L alone and CIITA+OX40-L showed decrease in EL4-specific CD8+ T cells compared to those at Day 20, percentage of EL4-specific CD8+ T cells in mice received EL4 expressing CIITA+4-1BB-L was maintained.

In order to evaluate induction of long-term memory T-cell response by the engineered cancer cells, mice that rejected EL4 overexpressing OX40-L+CIITA, 4-1BB-L+CIITA, or 4-1BB-L alone were rechallenged with the parental EL4 (FIG. 3A). Only a fraction of mice that rejected EL4 overexpressing 4-1BB-L alone or OX40-L+CIITA were resistant to the rechallenge (FIG. 3B). In contrast, all mice that rejected 4-1BB-L+CIITA rejected rechallenged EL4. 4-1BB-L-EL4 and 4-1BB-L+CIITA-EL4 induced comparable EL4-specific CD8+ T-cell response at early phase of immune response (FIG. 3D LEFT). In contrast, CD8+ T cells induced by 4-1BB-L+CIITA were maintained at later time point, compared to significant decrease in 4-1BB-L alone group (FIG. 3D RIGHT). Mice that rejected OX40-L+CIITA developed fewer EL4-specific CD8+ T cells at earlier time point and further decreased at later time point (FIG. 3D LEFT and RIGHT).

Figure 4:
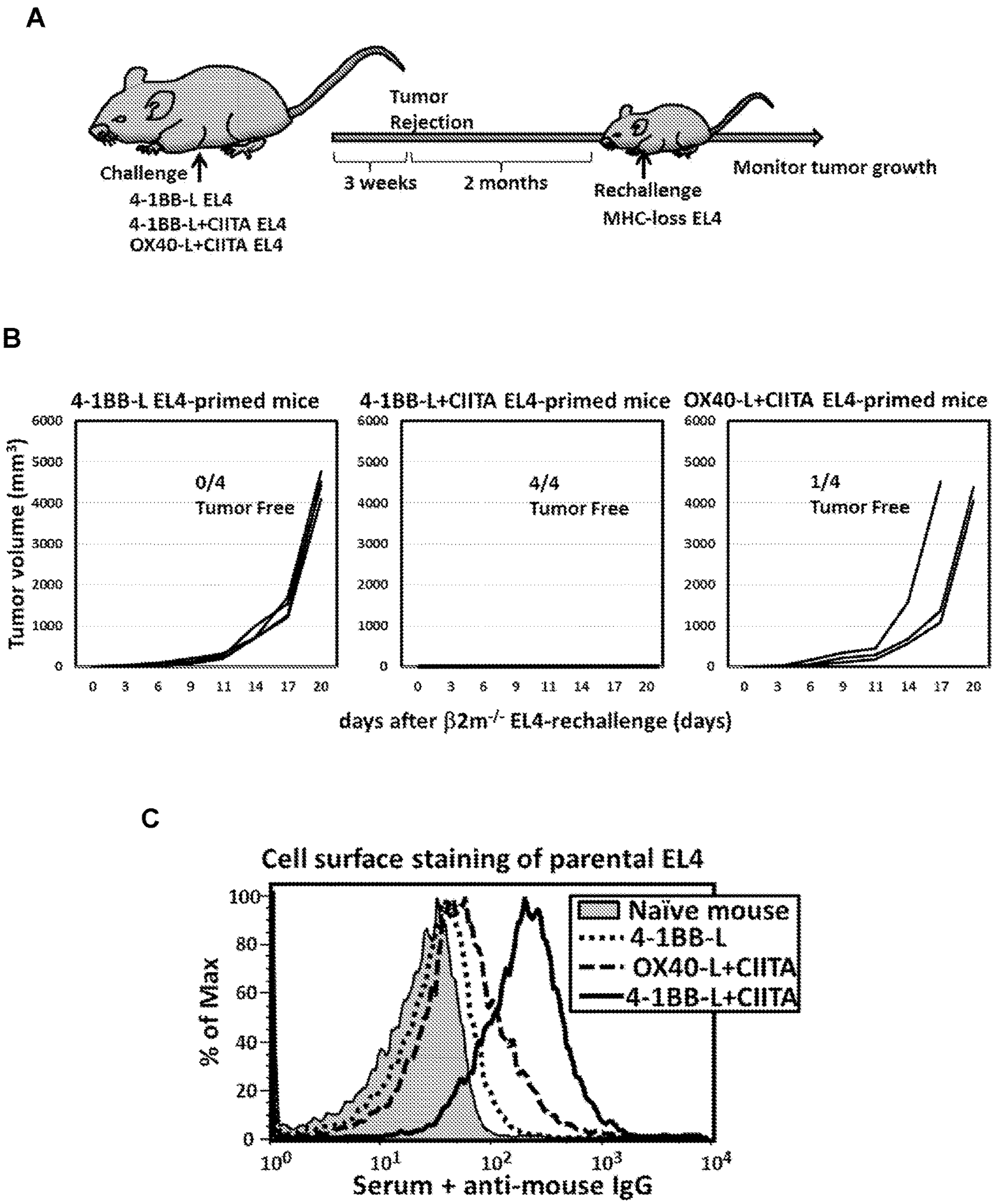
FIG. 4. Induction of antibody response by engineered cancer cells. (A) Experimental schema. To investigate protective antibody response, mice were first inoculated with EL4 engineered with 4-1BB-L alone, CIITA+4-1BB-L, or CIITA+OX40-L. Two months after complete regression, mice were subcutaneously re-challenged with EL4 engineered to silence MHC class I expression by disrupting b2m gene by CRISPR/Cas9 technology (b2m−/− EL4) and tumor growth was monitored. (B) Growth of MHC-loss EL4 (b2m−/− EL4) after rechallenge. Mice that initially rejected EL4-expressing 4-1BB-L alone or CIITA+OX40-L showed no or partial protection, respectively, against MHC-loss EL4. In contrast, all mice that initially received EL4-expressing CIITA+4-1BB-L rejected rechallenged MHC-loss EL4. (C) To investigate induction of antibodies against cell surface molecules on cancer cells, sera were collected from mice after they rejected engineered EL4 expressing 4-1BB-L alone, CIITA+4-1BB-L, or CIITA+OX40-L. The parental EL4 were first incubated with diluted serum and were stained with fluorescently labelled anti-mouse IgG antibody. Fluorescent intensity measured by flow cytometry is shown. (D) Fluorescent intensity was compared between treatment groups. Mice that rejected EL4 expressing CIITA+4-1BB-L or to the lesser extent EL4 expressing CIITA+OX40-L developed serum antibodies that bound on EL4. (E) The same sera from CIITA+4-1BB-L expressing EL4 rejected mice in (C) was used to stain irrelevant control cells such as activated murine T cells, B16F10 murine melanoma cell line and MC38 murine colon cancer cell line, indicating no cross-reactivity other than EL4. (F) Cytotoxicity by antibodies induced by engineered cancer cells. The parental EL4 were first loaded with fluorescent Calcein AM reagent, incubated with diluted serum, and were incubated with the rabbit complement. Cytotoxicity was calculated from fluorescent level in the supernatant.

In order to determine if the engineered cancer cells induce antitumor antibodies, mice that rejected EL4 overexpressing OX40-L+CIITA, 4-1BB-L+CIITA, and 4-1BB-L alone were rechallenged with EL4 that were engineered by CRISPR/Cas9 gene-editing to silence β2m gene and thus express no MHC molecule (MHC-loss EL4) (FIG. 4A). As shown in FIG. 4B, all mice that rejected 4-1BB+CIITA-expressing EL4 were resistant to rechallenge with MHC-loss EL4, whereas those rejected EL4 expressing 4-1BB-L alone or OX40-L+CIITA showed no or partial resistance, respectively (FIG. 4B). The presence of circulating EL4-reactive antibodies was tested by incubating the parental EL4 in diluted serum and by detecting immunoglobulin (IgG) bound on EL4 by fluorescent anti-mouse IgG antibody. EL4-expressing 4-1BB-L+CIITA induced significantly higher EL4-binding IgG response than EL4 expressing 4-1BB-L alone. In contrast, OX40-L+CIITA-expressing EL4 induced weaker antibody response (FIGS. 4C and 4D). Antibodies induced by EL4-expressing 4-1BB-L+CIITA were specific to EL4 as evidenced by control activated murine T cells, B16F10 melanoma, and MC38 colon cancer which were not stained by the serum (FIG. 4E). Antibodies induced by EL4-expressing 4-1BB-L+CIITA induced complement dependent cytotoxicity against EL4 (FIG. 4F).

Figure 5:
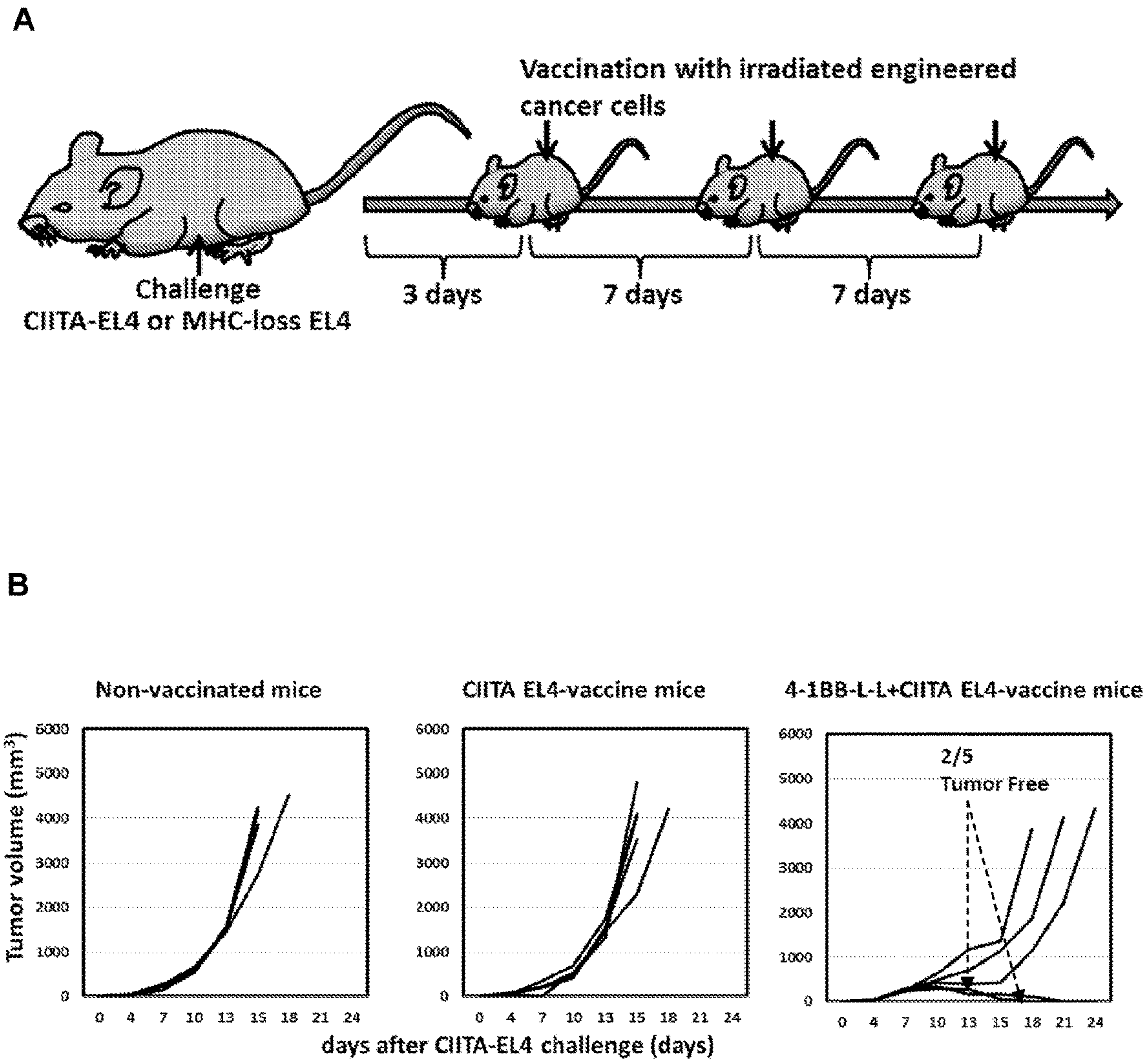
FIG. 5. Effect of therapeutic vaccination on tumor growth. (A) Experimental schema. Mice were first subcutaneously inoculated with EL4-expressing CIITA or MHC-loss EL4. On days 3, 10, and 17 mice were vaccinated with irradiated CIITA-EL4 or CIITA+4-1BB-L-EL4, or untreated. (B) Growth of CIITA-expressing EL4. There is no significant effect by vaccination with CIITA-EL4, tumor growth was significantly inhibited by CIITA+4-1BB-L-EL4. Two out of 5 mice completely rejected tumors. (C) Mice were first subcutaneously inoculated with MHC-loss EL4. On days 3, 10, and 17 mice were vaccinated with irradiated CIITA+4-1BB-L-EL4, or untreated. Mice that were vaccinated with CIITA+4-1BB-L-EL4 showed delayed tumor growth and 2 out of 7 mice completely rejected tumors. (D) Survival of mice in (C).

The therapeutic potential of engineered cancer cells was analyzed using a therapeutic vaccine model. In this model, CIITA overexpressing EL4 cells that express both MHC class I and MHC-II or MHC-loss EL4 were inoculated in C57BL/6 mice, and mice were vaccinated by irradiated engineered EL4 (FIG. 5A). Therapeutic vaccination with 4-1BB-L+CIITA-expressing EL4 induced significant antitumor effect including complete elimination in 2/5 mice (FIG. 5B). In addition, the same vaccination eliminated MHC-loss EL4 in 2/7 mice and prolonged survival of remaining mice (FIGS. 5C and 5D).

Figure 6:
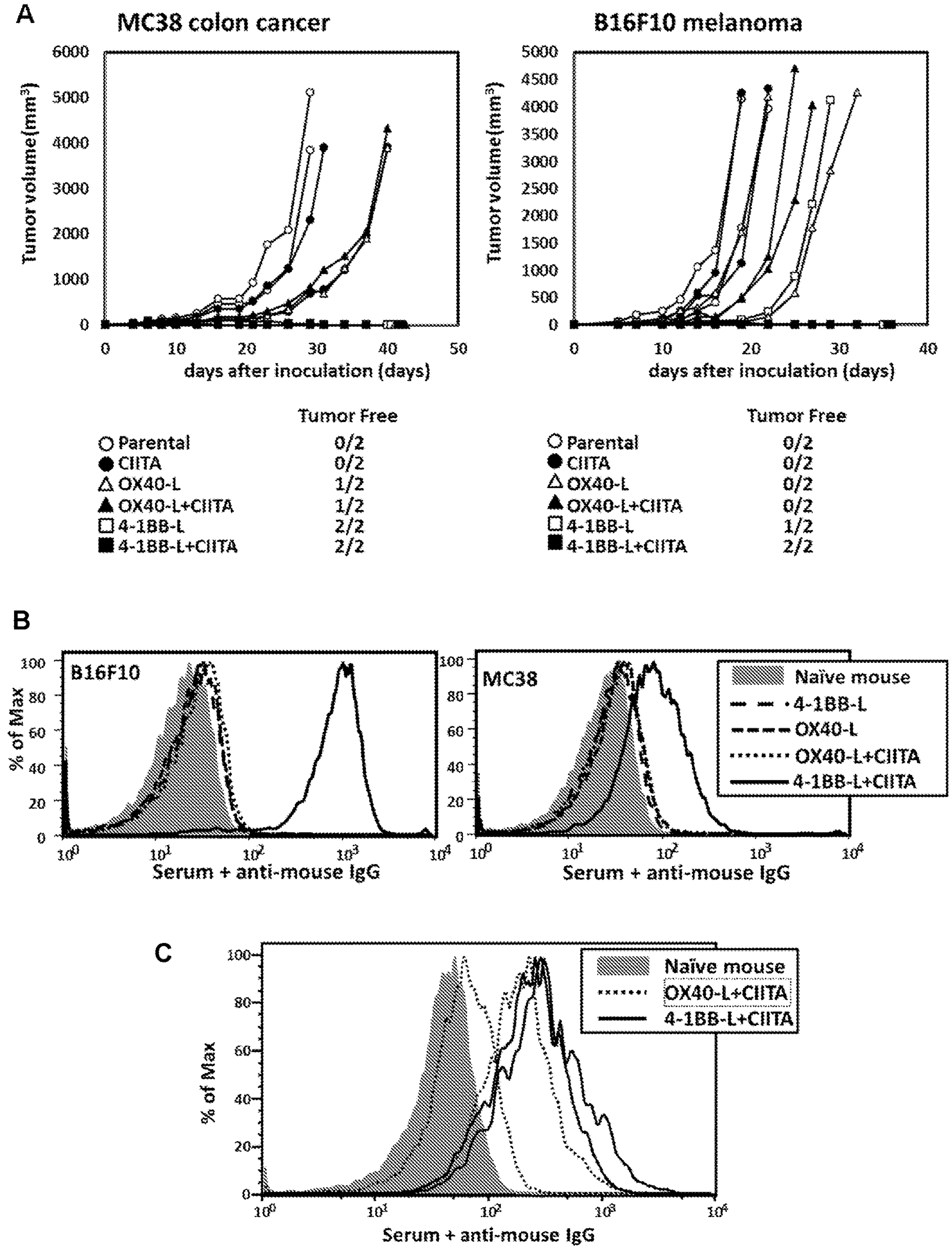
FIG. 6. Confirmation in other murine tumor models. (A) Mice were subcutaneously inoculated with MC38 colon cancer and B16F10 melanoma cell lines that were engineered to express the indicated genes. In both murine tumor models, co-expression of CIITA and 4-1BB-L induced spontaneous rejection. (B) Serum from mice in (A) were used to stain the parental MC38 and B16F10. Only mice that rejected engineered cancer cells expressing CIITA+4-1BB-L induced significant antibodies that bound on cell surface of cancer cells. (C) Induction of ovarian tumor-reactive antibody response by vaccination. Naïve mice were vaccinated with engineered murine ovarian cancer cell line, ID8, expressing CIITA+4-1BB-L or CIITA+OX40-L on days 0 and 7. Nineteen days after the second vaccination, sera were collected and used to stain the parental ID8 cell line. Both mice that were vaccinated with CIITA+4-1BB-L-ID8 induced ID8-reactive antibodies, whereas half of mice that received CIITA+OX40-L-ID8 induced significant ID8-reactive antibodies.

The effect of engineered cancer cells was tested in other tumor models. In both MC38 colon cancer and B16F10 melanoma models, 4-1BB-L+CIITA expressing cancer cells were spontaneously rejected in all mice (FIG. 6A), which was associated with higher circulating antibodies specific against respective cancers (FIG. 6B). Using murine ovarian cancer cell line, ID8, vaccination of mice with irradiated 4-1BB-L+CIITA-expressing ID8, and to a lesser extent OX40-L+CIITA-expressing ID8, induced antibodies that bound on the parental ID8 (FIG. 6C).

The following representative murine sequences were used to demonstrate embodiments of this disclosure. Those skilled in the art will recognize, given the benefit of this disclosure that the human sequences provide below the murine sequences, can be adapted for use in human cancer vaccines, and other therapeutic approaches based on the present disclosure.

Mouse

In DNA sequences, bold codons indicate the Start or Stop codon.

<CIITA>

>*Mus musculus* class II major histocompatibility complex transactivator (CIITA) (also known as "aka" C2ta; Gm9475; Mhc2ta; EG669998)

>DNA sequence (NCBI Reference Sequence: NM_001302618.1)

(SEQ ID NO: 1)

ATGAACCACTTCCAGGCCATCCTGGCCCAAGTACAGACACTGCTCTCCAG
CCAGAAGCCCAGGCAGGTGCGGGCCCTCCTGGATGGCCTGCTGGAAGAAG
AGCTGCTCTCACGGGAATACCACTGTGCCTTGCTGCATGAGCCTGATGGT
GATGCCCTGGCCCGGAAGATTTCCCTGACCCTGCTGGAGAAAGGGGACTT
AGACTTGACTTTCTTGAGCTGGGTCTGCAACAGTCTGCAGGCTCCCACGG
TAGAGAGGGGCACCAGCTACAGGGACCATGGAGACCATAGTCTGTGTGCC
ACCATGGATCTGGGATCTCCAGAGGGCAGCTACCTGGAACTCCTTAACAG
TGATGCCGACCCCCTACATCTCTACCACCTCTATGACCAGATGGACCTGG
CTGGGGAGGAGGAGATCGAACTCAGCTCAGAGCCAGACACAGATACCATC
AACTGCGACCAGTTCAGCAAGCTGTTGCAGGACATGGAACTGGATGAAGA
GACCCGGGAGGCCTATGCCAACATTGCGGAACTGGATCAGTACGTGTTCC
AGGATACCCAGCTCGAGGGCCTGAGCAAGGACCTCTTCATAGAGCACATT
GGAGCAGAGGAAGGCTTTGGTGAGAACATAGAGATCCCTGTAGAAGCAGG
ACAGAAGCCTCAGAAGAGACGCTTCCCGGAAGAGCATGCTATGGACTCAA
AGCACAGGAAGCTAGTGCCCACCTCTAGGACCTCACTGAACTATTTGGAT
CTCCCCACTGGGCACATCCAGATCTTCACCACTCTGCCCCAGGGACTCTG
GCAAATCTCAGGGGCTGGCACAGGTCTCTCCAGTGTCCTAATCTACCACG
GTGAGATGCCCCAGGTCAACCAAGTGCTCCCTTCAAGCAGCCTCAGTATC
CCCAGTCTCCCCGAGTCCCCAGACCGGCCTGGCTCCACCAGCCCCTTCAC
ACCATCTGCAGCTGACCTGCCCAGCATGCCCGAACCTGCGCTGACCTCCC
GTGTAAATGAGACAGAGGACACATCTCCCTCCCCATGCCAAGAGGGTCCC
GAGTCTTCCATCAAGCTTCCAAAATGGCCAGAGGCTGTGGAGCGATTCCA
GCACTCCCTACAGGACAAATACAAGGCATTGCCCCAGAGCCCAAGGGGTC
CTCTGGTGGCCGTGGAGCTGGTACGGGCCAGGCTGGAAAGAGGCAGCAAC
AAGAGCCAGGAAAGGGAGCTGGCCACTCCCGACTGGACAGAGCGCCAGCT
AGCCCACGGTGGTCTGGCAGAGGTACTTCAGGTTGTCAGTGACTGCAGGC
GACCAGGAGAGACACAGGTGGTCGCTGTGCTGGGCAAGGCTGGCCAGGGA
AAGAGCCACTGGGCCAGGACAGTGAGTCACACCTGGGCATGTGGCCAGTT
GCTACAATATGACTTTGTCTTCTATGTCCCCTGTCATTGCTTGGATCGTC
CCGGGGACACCTACCACCTGCGGGATCTGCTCTGTCCCCCGAGCCTGCAG
CCACTGGCCATGGATGACGAGGTCCTTGATTATATCGTGAGGCAGCCAGA
CCGTGTTCTGCTCATCCTAGATGCTTTCGAGGAGCTAGAGGCCCAAGATG
GCCTCCTGCACGGACCCTGTGGATCTCTGTCCCCAGAGCCCTGCTCCCTC
CGAGGACTGCTGGCTGGGATCTTCCAGCGGAAGCTACTGCGAGGCTGCAC
ACTGCTCCTCACAGCCCGGCCCCGGGGCCGCCTGGCTCAGAGCCTGAGCA
AGGCAGATGCCATCTTTGAGGTGCCCAGCTTCTCTACCAAGCAGGCCAAG

-continued

ACTTACATGAGGCACTACTTTGAGAACTCAGGGACAGCGGGGAACCAAGA
CAAGGCCCTGGGCCTCCTGGAGGGCCAGCCTCTTCTCTGCAGCTATAGTC
ACAGCCCTGTTGTGTGCAGGGCTGTGTGCCAGCTCTCCAAGGCCCTGCTA
GAACAGGGCACAGAGGCCCAGCTACCTTGTACACTTACAGGACTCTATGT
CAGCCTGCTAGGTCCTGCAGCTCAGAACAGTCCTCCCGGAGCCTTAGTCG
AGCTGGCCAAGCTGGCCTGGGAGCTGGGACGAAGACACCAAAGCACCTTG
CAAGAAACCCGGTTTTCATCCGTGGAGGTGAAAACCTGGGCAGTGACCCA
AGGCTTGATGCAGCAGACCCTGGAGACCACGGAGGCTCAACTGGCCTTCT
CCAGTTTTCTGCTACAGTGTTTCCTGGGTGCTGTGTGGCTGGCACAGTGC
AATGAAATCAAAGACAAGGAGCTGCCACAGTACCTGGCCTTGACTCCGAG
GAAGAAGAGACCCTATGACAACTGGCTGGAGGGTGTACCACGCTTTCTGG
CTGGATTAGTTTTCCAGCCTCGAGCCCACTGCCTGGGAGCTCTGGTGGAG
CCTGCAGTGGCTGCAGTGGCGGATAGGAAACAGAAGGTTCTTACCAGGTA
CCTGAAGCGCCTGAAGCTGGGGACACTCCGGGCAGGGAGGCTGCTGGAGC
TGCTCCACTGTGCCCACGAGACACAGCAACCTGGGATATGGGAGCATGTT
GCACACCAGCTCCCTGGCCACCTCTCCTTCCTGGGCACCCGGCTCACACC
CCCAGATGTGTATGTGCTGGGCAGGGCCTTGGAGACAGCCAGCCAGGACT
TCTCCTTGGACCTTCGTCAGACTGGCGTTGAGCCTTCTGGACTGGGAAAC
CTCGTGGGACTCAGCTGTGTCACCAGTTTCAGGGCCTCCTTGAGTGATAC
AATGGCATTATGGGAGTCCCTTCAGCAGCAGGGAGAAGCCCAGCTACTCC
AGGCGGCAGAGGAGAAGTTCACCATTGAGCCATTTAAAGCCAAATCCCCA
AAGGATGTGGAAGACCTGGATCGTCTCGTGCAGACCCAGAGGCTGAGAAA
CCCCTCAGAAGATGCAGCCAAGGATCTTCCTGCCATCCGGGACCTTAAGA
AGCTAGAGTTTGCGTTGGGCCCCATCTTGGGCCCCCAGGCTTTCCCCACA
CTGGCAAAGATCCTTCCAGCCTTCTCTTCTCTGCAACACCTGGACCTGGA
CTCACTTAGTGAGAACAAGATCGGAGACAAGGGTGTGTCGAAGCTCTCAG
CCACCTTCCCTCAGCTGAAGGCCCTGGAGACGCTCAACTTGTCCCAAAAC
AACATCACTGATGTGGGTGCCTGCAAGCTTGCAGAAGCTCTGCCAGCCCT
AGCCAAGTCCCTCCTAAGGCTGAGCTTGTACAATAACTGCATCTGTGACA
AAGGAGCCAAGAGCCTGGCACAAGTACTTCCGGACATGGTGTCCCTGCGT
GTGATGGATGTCCAGTTCAACAAGTTCACGGCTGCCGGTGCCCAGCAACT
GGCCTCCAGCCTTCAGAAGTGCCCTCAGGTGGAAACACTGGCAATGTGGA
CACCCACTATCCCCTTTGGGGTTCAGGAACACCTGCAGCAGCTGGATGCC
AGGATCAGTCTGAGATGA

CIITA Protein sequence (NCBI Reference Sequence: NP_001289547.1)

(SEQ ID NO: 2)

MNHFQAILAQVQTLLSSQKPRQVRALLDGLLEEELLSREYHCALLHEPDG
DALARKISLTLLEKGDLDLTFLSWVCNSLQAPTVERGTSYRDHGDHSLCA
TMDLGSPEGSYLELLNSDADPLHLYHLYDQMDLAGEEEIELSSEPDTDTI

-continued

NCDQFSKLLQDMELDEETREAYANIAELDQYVFQDTQLEGLSKDLFIEHI
GAEEGFGENIEIPVEAGQKPQKRRFPEEHAMDSKHRKLVPTSRTSLNYLD
LPTGHIQIFTTLPQGLWQISGAGTGLSSVLIYHGEMPQVNQVLPSSSLSI
PSLPESPDRPGSTSPFTPSAADLPSMPEPALTSRVNETEDTSPSPCQEGP
ESSIKLPKWPEAVERFQHSLQDKYKALPQSPRGPLVAVELVRARLERGSN
KSQERELATPDWTERQLAHGGLAEVLQVVSDCRRPGETQVVAVLGKAGQG
KSHWARTVSHTWACGQLLQYDFVFYVPCHCLDRPGDTYHLRDLLCPPSLQ
PLAMDDEVLDYIVRQPDRVLLILDAFEELEAQDGLLHGPCGSLSPEPCSL
RGLLAGIFQRKLLRGCTLLLTARPRGRLAQSLSKADAIFEVPSFSTKQAK
TYMRHYFENSGTAGNQDKALGLLEGQPLLCSYSHSPVVCRAVCQLSKALL
EQGTEAQLPCTLTGLYVSLLGPAAQNSPPGALVELAKLAWELGRRHQSTL
QETRFSSVEVKTWAVTQGLMQQTLETTEAQLAFSSFLLQCFLGAVWLAQC
NEIKDKELPQYLALTPRKKRPYDNWLEGVPRFLAGLVFQPRAHCLGALVE
PAVAAVADRKQKVLTRYLKRLKLGTLRAGRLLELLHCAHETQQPGIWEHV
AHQLPGHLSFLGTRLTPPDVYVLGRALETASQDFSLDLRQTGVEPSGLGN
LVGLSCVTSFRASLSDTMALWESLQQQGEAQLLQAAEEKFTIEPFKAKSP
KDVEDLDRLVQTQRLRNPSEDAAKDLPAIRDLKKLEFALGPILGPQAFPT
LAKILPAFSSLQHLDLDSLSENKIGDKGVSKLSATFPQLKALETLNLSQN
NITDVGACKLAEALPALAKSLLRLSLYNNCICDKGAKSLAQVLPDMVSLR
VMDVQFNKFTAAGAQQLASSLQKCPQVETLAMWTPTIPFGVQEHLQQLDA
RISLR

<4-1BB-L>

>TNFSF9: TNF superfamily member 9 (aka Ly631; 4-1BBL; Cd1371; 4-1BB-L; AI848817)

>DNA sequence (NCBI Reference Sequence: NM_009404.3)

(SEQ ID NO: 3)

ATGGACCAGCACACACTTGATGTGGAGGATACCGCGGATGCCAGACATCC
AGCAGGTACTTCGTGCCCCTCGGATGCGGCGCTCCTCAGAGATACCGGGC
TCCTCGCGGACGCTGCGCTCCTCTCAGATACTGTGCGCCCCACAAATGCC
GCGCTCCCCACGGATGCTGCCTACCCTGCGGTTAATGTTCGGGATCGCGA
GGCCGCGTGGCCGCCTGCACTGAACTTCTGTTCCCGCCACCCAAAGCTCT
ATGGCCTAGTCGCTTTGGTTTTGCTGCTTCTGATCGCCGCCTGTGTTCCT
ATCTTCACCCGCACCGAGCCTCGGCCAGCGCTCACAATCACCACCTCGCC
CAACCTGGGTACCCGAGAGAATAATGCAGACCAGGTCACCCCTGTTTCCC
ACATTGGCTGCCCCAACACTACACAACAGGGCTCTCCTGTGTTCGCCAAG
CTACTGGCTAAAAACCAAGCATCGTTGTGCAATACAACTCTGAACTGGCA
CAGCCAAGATGGAGCTGGGAGCTCATACCTATCTCAAGGTCTGAGGTACG
AAGAAGACAAAAAGGAGTTGGTGGTAGACAGTCCCGGGCTCTACTACGTA
TTTTTGGAACTGAAGCTCAGTCCAACATTCACAAACACAGGCCACAAGGT
GCAGGGCTGGGTCTCTCTTGTTTTGCAAGCAAAGCCTCAGGTAGATGACT
TTGACAACTTGGCCCTGACAGTGGAACTGTTCCCTTGCTCCATGGAGAAC

-continued

AAGTTAGTGGACCGTTCCTGGAGTCAACTGTTGCTCCTGAAGGCTGGCCA
CCGCCTCAGTGTGGGTCTGAGGGCTTATCTGCATGGAGCCCAGGATGCAT
ACAGAGACTGGGAGCTGTCTTATCCCAACACCACCAGCTTTGGACTCTTT
CTTGTGAAACCCGACAACCCATGGGAATGA

4-1BB-L Protein sequence (NCBI Reference Sequence: NP_033430.1)

(SEQ ID NO: 4)

MDQHTLDVEDTADARHPAGTSCPSDAALLRDTGLLADAALLSDTVRPTNA
ALPTDAAYPAVNVRDREAAWPPALNFCSRHPKLYGLVALVLLLLIAACVP
IFTRTEPRPALTITTSPNLGTRENNADQVTPVSHIGCPNTTQQGSPVFAK
LLAKNQASLCNTTLNWHSQDGAGSSYLSQGLRYEEDKKELVVDSPGLYYV
FLELKLSPTFTNTGHKVQGWVSLVLQAKPQVDDFDNLALTVELFPCSMEN
KLVDRSWSQLLLLKAGHRLSVGLRAYLHGAQDAYRDWELSYPNTTSFGLF
LVKPDNPWE

<OX40-L>

>TNFSF4: TNF superfamily member 4 (aka Ath1; gp34; Ath-1; Ox40l; TXGP1; CD134L; OX-40L; Tnlg2b; Txgp11)

>DNA sequence (NCBI Reference Sequence: NM_009452.2)

(SEQ ID NO: 5)

ATGGAAGGGGAAGGGGTTCAACCCCTGGATGAGAATCTGGAAAACGGATC
AAGGCCAAGATTCAAGTGGAAGAAGACGCTAAGGCTGGTGGTCTCTGGGA
TCAAGGGAGCAGGGATGCTTCTGTGCTTCATCTATGTCTGCCTGCAACTC
TCTTCCTCTCCGGCAAAGGACCCTCCAATCCAAAGACTCAGAGGAGCAGT
TACCAGATGTGAGGATGGGCAACTATTCATCAGCTCATACAAGAATGAGT
ATCAAACTATGGAGGTGCAGAACAATTCGGTTGTCATCAAGTGCGATGGG
CTTTATATCATCTACCTGAAGGGCTCCTTTTTCCAGGAGGTCAAGATTGA
CCTTCATTTCCGGGAGGATCATAATCCCATCTCTATTCCAATGCTGAACG
ATGGTCGAAGGATTGTCTTCACTGTGGTGGCCTCTTTGGCTTTCAAAGAT
AAAGTTTACCTGACTGTAAATGCTCCTGATACTCTCTGCGAACACCTCCA
GATAAATGATGGGGAGCTGATTGTTGTCCAGCTAACGCCTGGATACTGTG
CTCCTGAAGGATCTTACCACAGCACTGTGAACCAAGTACCACTGTGA

>OX40-L Protein sequence (NCBI Reference Sequence: NP_033478.1)

(SEQ ID NO: 6)

MEGEGVQPLDENLENGSRPRFKWKKTLRLVVSGIKGAGMLLCFIYVCLQL
SSSPAKDPPIQRLRGAVTRCEDGQLFISSYKNEYQTMEVQNNSVVIKCDG
LYIIYLKGSFFQEVKIDLHFREDHNPISIPMLNDGRRIVFTVVASLAFKD
KVYLTVNAPDTLCEHLQINDGELIVVQLTPGYCAPEGSYHSTVNQVPL

<GITR-L>

>TNFSF18 TNF superfamily member 18 (aka Gitr1; Tnlg2a)

>DNA sequence (NCBI Reference Sequence: NM_183391.3)

(SEQ ID NO: 7)
ATGGAGGAAATGCCTTTGAGAGAATCAAGTCCTCAAAGGGCAGAGAGGTG
CAAGAAGTCATGGCTCTTGTGCATAGTGGCTCTGTTACTGATGTTGCTCT
GTTCTTTGGGTACACTGATCTATACTTCACTCAAGCCAACTGCCATCGAG
TCCTGCATGGTTAAGTTTGAACTATCATCCTCAAAATGGCACATGACATC
TCCCAAACCTCACTGTGTGAATACGACATCTGATGGGAAGCTGAAGATAC
TGCAGAGTGGCACATATTTAATCTACGGCCAAGTGATTCCTGTGGATAAG
AAATACATAAAAGACAATGCCCCCTTCGTAGTACAGATATATAAAAAGAA
TGATGTCCTACAAACTCTAATGAATGATTTTCAAATCTTGCCTATAGGAG
GGGTTTATGAACTGCATGCTGGAGATAACATATATCTGAAGTTCAACTCT
AAAGACCATATTCAGAAAACTAACACATACTGGGGGATCATCTTAATGCC
TGATCTACCATTCATCTCTTAG

>TNFSF18 Protein sequence (NCBI Reference Sequence: NP_899247.3)

(SEQ ID NO: 8)
MEEMPLRESSPQRAERCKKSWLLCIVALLLMLLCSLGTLIYTSLKPTAIE
SCMVKFELSSSKWHMTSPKPHCVNTTSDGKLKILQSGTYLIYGQVIPVDK
KYIKDNAPFVVQIYKKNDVLQTLMNDFQILPIGGVYELHAGDNIYLKFNS
KDHIQKTNTYWGIILMPDLPFIS

<CD80>

>CD80 (aka B71; Ly53; TSA1; Cd281; Ly-53; MIC17)

>DNA sequence (NCBI Reference Sequence: NM_001359898.1)

(SEQ ID NO: 9)
ATGGCTTGCAATTGTCAGTTGATGCAGGATACACCACTCCTCAAGTTTCC
ATGTCCAAGGCTCATTCTTCTCTTTGTGCTGCTGATTCGTCTTTCACAAG
TGTCTTCAGATGTTGATGAACAACTGTCCAAGTCAGTGAAAGATAAGGTA
TTGCTGCCTTGCCGTTACAACTCTCCTCATGAAGATGAGTCTGAAGACCG
AATCTACTGGCAAAAACATGACAAAGTGGTGCTGTCTGTCATTGCTGGGA
AACTAAAAGTGTGGCCCGAGTATAAGAACCGGACTTTATATGACAACACT
ACCTACTCTCTTATCATCCTGGGCCTGGTCCTTTCAGACCGGGGCACATA
CAGCTGTGTCGTTCAAAAGAAGGAAAGAGGAACGTATGAAGTTAAACACT
TGGCTTTAGTAAAGTTGTCCATCAAAGCTGACTTCTCTACCCCCAACATA
ACTGAGTCTGGAAACCCATCTGCAGACACTAAAAGGATTACCTGCTTTGC
TTCCGGGGGTTTCCCAAAGCCTCGCTTCTCTTGGTTGGAAAATGGAAGAG
AATTACCTGGCATCAATACGACAATTTCCCAGGATCCTGAATCTGAATTG
TACACCATTAGTAGCCAACTAGATTTCAATACGACTCGCAACCACACCAT
TAAGTGTCTCATTAAATATGGAGATGCTCACGTGTCAGAGGACTTCACCT
GGGAAAAACCCCCAGAAGACCCTCCTGATAGCAAGAACACACTTGTGCTC
TTTGGGGCAGGATTCGGCGCAGTAATAACAGTCGTCGTCATCGTTGTCAT
CATCAAATGCTTCTGTAAGCACAGAAGCTGTTTCAGAAGAAATGAGGCAA

-continued

GCAGAGAAACAAACAACAGCCTTACCTTCGGGCCTGAAGAAGCATTAGCT
GAACAGACCGTCTTCCTTTAG

>CD80 Protein Sequence (NCBI Reference Sequence: NP_001346827.1)

(SEQ ID NO: 10)
MACNCQLMQDTPLLKFPCPRLILLFVLLIRLSQVSSDVDEQLSKSVKDK
VLLPCRYNSPHEDESEDRIYWQKHDKVVLSVIAGKLKVWPEYKNRTLYD
NTTYSLIILGLVLSDRGTYSCVVQKKERGTYEVKHLALVKLSIKADFST
PNITESGNPSADTKRITCFASGGFPKPRFSWLENGRELPGINTTISQDP
ESELYTISSQLDFNTTRNHTIKCLIKYGDAHVSEDFTWEKPPEDPPDSK
NTLVLFGAGFGAVITVVVIVVIIKCFCKHRSCFRRNEASRETNNSLTFG
PEEALAEQTVFL

<GM-CSF>

>CSF2: colony stimulating factor 2 (aka CSF; Csfgm; GMCSF; Gm-CSf; MGI-IGM)

>DNA sequence (NCBI Reference Sequence: NM_009969.4)

(SEQ ID NO: 11)
ATGTGGCTGCAGAATTTACTTTTCCTGGGCATTGTGGTCTACAGCCTCT
CAGCACCCACCCGCTCACCCATCACTGTCACCCGGCCTTGGAAGCATGT
AGAGGCCATCAAAGAAGCCCTGAACCTCCTGGATGACATGCCTGTCACG
TTGAATGAAGAGGTAGAAGTCGTCTCTAACGAGTTCTCCTTCAAGAAGC
TAACATGTGTGCAGACCCGCCTGAAGATATTCGAGCAGGGTCTACGGGG
CAATTTCACCAAACTCAAGGGCGCCTTGAACATGACAGCCAGCTACTAC
CAGACATACTGCCCCCCAACTCCGGAAACGGACTGTGAAACACAAGTTA
CCACCTATGCGGATTTCATAGACAGCCTTAAAACCTTTCTGACTGATAT
CCCCTTTGAATGCAAAAAACCAGGCCAAAAATGA

>GM-CSF Protein sequence (NCBI Reference Sequence: NP_034099.2)

(SEQ ID NO: 12)
MWLQNLLFLGIVVYSLSAPTRSPITVTRPWKHVEAIKEALNLLDDMPVT
LNEEVEVVSNEFSFKKLTCVQTRLKIFEQGLRGNFTKLKGALNMTASYY
QTYCPPTPETDCETQVTTYADFIDSLKTFLTDIPFECKKPGQK

Human

In the following DNA sequences, bold codons indicate the Start or Stop codon.

<CIITA>

>*Homo sapiens* class II major histocompatibility complex transactivator (CIITA) (also known in the art as C2TA; NLRA; MHC2TA; CIITAIV)

>DNA sequence (NCBI Reference Sequence: NM_001286402.1)

(SEQ ID NO: 13)
ATGCGTTGCCTGGCTCCACGCCCTGCTGGGTCCTACCTGTCAGAGCCCC

-continued

AAGGCAGCTCACAGTGTGCCACCATGGAGTTGGGGCCCCTAGAAGGTGG

CTACCTGGAGCTTCTTAACAGCGATGCTGACCCCCTGTGCCTCTACCAC

TTCTATGACCAGATGGACCTGGCTGGAGAAGAAGAGATTGAGCTCTACT

CAGAACCCGACACAGACACCATCAACTGCGACCAGTTCAGCAGGCTGTT

GTGTGACATGGAAGGTGATGAAGAGACCAGGGAGGCTTATGCCAATATC

GCGGAACTGGACCAGTATGTCTTCCAGGACTCCCAGCTGGAGGGCCTGA

GCAAGGACATTTTCATAGAGCACATAGGACCAGATGAAGTGATCGGTGA

GAGTATGGAGATGCCAGCAGAAGTTGGGCAGAAAAGTCAGAAAAGACCC

TTCCCAGAGGAGCTTCCGGCAGACCTGAAGCACTGGAAGCCAGCTGAGC

CCCCCACTGTGGTGACTGGCAGTCTCCTAGTGGGACCAGTGAGCGACTG

CTCCACCCTGCCCTGCCTGCCACTGCCTGCGCTGTTCAACCAGGAGCCA

GCCTCCGGCCAGATGCGCCTGGAGAAAACCGACCAGATTCCCATGCCTT

TCTCCAGTTCCTCGTTGAGCTGCCTGAATCTCCCTGAGGGACCCATCCA

GTTTGTCCCCACCATCTCCACTCTGCCCCATGGGCTCTGGCAAATCTCT

GAGGCTGGAACAGGGGTCTCCAGTATATTCATCTACCATGGTGAGGTGC

CCCAGGCCAGCCAAGTACCCCCTCCCAGTGGATTCACTGTCCACGGCCT

CCCAACATCTCCAGACCGGCCAGGCTCCACCAGCCCCTTCGCTCCATCA

GCCACTGACCTGCCCAGCATGCCTGAACCTGCCCTGACCTCCCGAGCAA

ACATGACAGAGCACAAGACGTCCCCCACCCAATGCCCGGCAGCTGGAGA

GGTCTCCAACAAGCTTCCAAAATGGCCTGAGCCGGTGGAGCAGTTCTAC

CGCTCACTGCAGGACACGTATGGTGCCGAGCCCGCAGGCCCGGATGGCA

TCCTAGTGGAGGTGGATCTGGTGCAGGCCAGGCTGGAGAGGAGCAGCAG

CAAGAGCCTGGAGCGGGAACTGGCCACCCCGGACTGGGCAGAACGGCAG

CTGGCCCAAGGAGGCCTGGCTGAGGTGCTGTTGGCTGCCAAGGAGCACC

GGCGGCCGCGTGAGACACGAGTGATTGCTGTGCTGGGCAAAGCTGGTCA

GGGCAAGAGCTATTGGGCTGGGGCAGTGAGCCGGGCCTGGGCTTGTGGC

CGGCTTCCCCAGTACGACTTTGTCTTCTCTGTCCCCTGCCATTGCTTGA

ACCGTCCGGGGGATGCCTATGGCCTGCAGGATCTGCTCTTCTCCCTGGG

CCCACAGCCACTCGTGGCGGCCGATGAGGTTTTCAGCCACATCTTGAAG

AGACCTGACCGCGTTCTGCTCATCCTAGACGGCTTCGAGGAGCTGGAAG

CGCAAGATGGCTTCCTGCACAGCACGTGCGGACCGGCACCGGCGGAGCC

CTGCTCCCTCCGGGGGCTGCTGGCCGGCCTTTTCCAGAAGAAGCTGCTC

CGAGGTTGCACCCTCCTCCTCACAGCCCGGCCCCGGGGCCGCCTGGTCC

AGAGCCTGAGCAAGGCCGACGCCCTATTTGAGCTGTCCGGCTTCTCCAT

GGAGCAGGCCCAGGCATACGTGATGCGCTACTTTGAGAGCTCAGGGATG

ACAGAGCACCAAGACAGAGCCCTGACGCTCCTCCGGGACCGGCCACTTC

TTCTCAGTCACAGCCACAGCCCTACTTTGTGCCGGGCAGTGTGCCAGCT

CTCAGAGGCCCTGCTGGAGCTTGGGGAGGACGCCAAGCTGCCCTCCACG

CTCACGGGACTCTATGTCGGCCTGCTGGGCCGTGCAGCCCTCGACAGCC

CCCCCGGGGCCCTGGCAGAGCTGGCCAAGCTGGCCTGGGAGCTGGGCCG

CAGACATCAAAGTACCCTACAGGAGGACCAGTTCCCATCCGCAGACGTG

AGGACCTGGGCGATGGCCAAAGGCTTAGTCCAACACCCACCGCGGGCCG

CAGAGTCCGAGCTGGCCTTCCCCAGCTTCCTCCTGCAATGCTTCCTGGG

GGCCCTGTGGCTGGCTCTGAGTGGCGAAATCAAGGACAAGGAGCTCCCG

CAGTACCTAGCATTGACCCCAAGGAAGAAGAGGCCCTATGACAACTGGC

TGGAGGGCGTGCCACGCTTTCTGGCTGGGCTGATCTTCCAGCCTCCCGC

CCGCTGCCTGGGAGCCCTACTCGGGCCATCGGCGGCTGCCTCGGTGGAC

AGGAAGCAGAAGGTGCTTGCGAGGTACCTGAAGCGGCTGCAGCCGGGGA

CACTGCGGGCGCGGCAGCTGCTGGAGCTGCTGCACTGCGCCCACGAGGC

CGAGGAGGCTGGAATTTGGCAGCACGTGGTACAGGAGCTCCCCGGCCGC

CTCTCTTTTCTGGGCACCCGCCTCACGCCTCCTGATGCACATGTACTGG

GCAAGGCCTTGGAGGCGGCGGGCCAAGACTTCTCCCTGGACCTCCGCAG

CACTGGCATTTGCCCCTCTGGATTGGGGAGCCTCGTGGGACTCAGCTGT

GTCACCCGTTTCAGGGCTGCCTTGAGCGACACGGTGGCGCTGTGGGAGT

CCCTGCAGCAGCATGGGGAGACCAAGCTACTTCAGGCAGCAGAGGAGAA

GTTCACCATCGAGCCTTTCAAAGCCAAGTCCCTGAAGGATGTGGAAGAC

CTGGGAAAGCTTGTGCAGACTCAGAGGACGAGAAGTTCCTCGGAAGACA

CAGCTGGGGAGCTCCCTGCTGTTCGGGACCTAAAGAAACTGGAGTTTGC

GCTGGGCCCTGTCTCAGGCCCCCAGGCTTTCCCCAAACTGGTGCGGATC

CTCACGGCCTTTTCCTCCCTGCAGCATCTGGACCTGGATGCGCTGAGTG

AGAACAAGATCGGGGACGAGGGTGTCTCGCAGCTCTCAGCCACCTTCCC

CCAGCTGAAGTCCTTGGAAACCCTCAATCTGTCCCAGAACAACATCACT

GACCTGGGTGCCTACAAACTCGCCGAGGCCCTGCCTTCGCTCGCTGCAT

CCCTGCTCAGGCTAAGCTTGTACAATAACTGCATCTGCGACGTGGGAGC

CGAGAGCTTGGCTCGTGTGCTTCCGGACATGGTGTCCCTCCGGGTGATG

GACGTCCAGTACAACAAGTTCACGGCTGCCGGGGCCCAGCAGCTCGCTG

CCAGCCTTCGGAGGTGTCCTCATGTGGAGACGCTGGCGATGTGGACGCC

CACCATCCCATTCAGTGTCCAGGAACACCTGCAACAACAGGATTCACGG

ATCAGCCTGAGATGA

>Human CIITA Protein sequence (NCBI Reference Sequence: NP_001273331.1)

(SEQ ID NO: 14)

MRCLAPRPAGSYLSEPQGSSQCATMELGPLEGGYLELLNSDADPLCLYH

FYDQMDLAGEEEIELYSEPDTDTINCDQFSRLLCDMEGDEETREAYANI

AELDQYVFQDSQLEGLSKDIFIEHIGPDEVIGESMEMPAEVGQKSQKRP

FPEELPADLKHWKPAEPPTVVTGSLLVGPVSDCSTLPCLPLPALFNQEP

ASGQMRLEKTDQIPMPFSSSSLSCLNLPEGPIQFVPTISTLPHGLWQIS

EAGTGVSSIFIYHGEVPQASQVPPPSGFTVHGLPTSPDRPGSTSPFAPS

ATDLPSMPEPALTSRANMTEHKTSPTQCPAAGEVSNKLPKWPEPVEQFY

RSLQDTYGAEPAGPDGILVEVDLVQARLERSSSKSLERELATPDWAERQ

LAQGGLAEVLLAAKEHRRPRETRVIAVLGKAGQGKSYWAGAVSRAWACG

-continued

RLPQYDFVFSVPCHCLNRPGDAYGLQDLLFSLGPQPLVAADEVFSHILK

RPDRVLLILDGFEELEAQDGFLHSTCGPAPAEPCSLRGLLAGLFQKKLL

RGCTLLLTARPRGRLVQSLSKADALFELSGFSMEQAQAYVMRYFESSGM

TEHQDRALTLLRDRPLLLSHSHSPTLCRAVCQLSEALLELGEDAKLPST

LTGLYVGLLGRAALDSPPGALAELAKLAWELGRRHQSTLQEDQFPSADV

RTWAMAKGLVQHPPRAAESELAFPSFLLQCFLGALWLALSGEIKDKELP

QYLALTPRKKRPYDNWLEGVPRFLAGLIFQPPARCLGALLGPSAAASVD

RKQKVLARYLKRLQPGTLRARQLLELLHCAHEAEEAGIWQHVVQELPGR

LSFLGTRLTPPDAHVLGKALEAAGQDFSLDLRSTGICPSGLGSLVGLSC

VTRFRAALSDTVALWESLQQHGETKLLQAAEEKFTIEPFKAKSLKDVED

LGKLVQTQRTRSSSEDTAGELPAVRDLKKLEFALGPVSGPQAFPKLVRI

LTAFSSLQHLDLDALSENKIGDEGVSQLSATFPQLKSLETLNLSQNNIT

DLGAYKLAEALPSLAASLLRLSLYNNCICDVGAESLARVLPDMVSLRVM

DVQYNKFTAAGAQQLAASLRRCPHVETLAMWTPTIPFSVQEHLQQQDSR

ISLR

<4-1BB-L>

>Human TNFSF9: TNF superfamily member 9 (aka CD137L; TNLG5A; 4-1BB-L)

>DNA sequence (NCBI Reference Sequence: NM_003811.3)

(SEQ ID NO: 15)

ATGGAATACGCCTCTGACGCTTCACTGGACCCCGAAGCCCCGTGGCCTC

CCGCGCCCCGCGCTCGCGCCTGCCGCGTACTGCCTTGGGCCCTGGTCGC

GGGGCTGCTGCTGCTGCTGCTCGCTGCCGCCTGCGCCGTCTTCCTC

GCCTGCCCCTGGGCCGTGTCCGGGGCTCGCGCCTCGCCCGGCTCCGCGG

CCAGCCCGAGACTCCGCGAGGGTCCCGAGCTTTCGCCCGACGATCCCGC

CGGCCTCTTGGACCTGCGGCAGGGCATGTTTGCGCAGCTGGTGGCCCAA

AATGTTCTGCTGATCGATGGGCCCCTGAGCTGGTACAGTGACCCAGGCC

TGGCAGGCGTGTCCCTGACGGGGGGCCTGAGCTACAAAGAGGACACGAA

GGAGCTGGTGGTGGCCAAGGCTGGAGTCTACTATGTCTTCTTTCAACTA

GAGCTGCGGCGCGTGGTGGCCGGCGAGGGCTCAGGCTCCGTTTCACTTG

CGCTGCACCTGCAGCCACTGCGCTCTGCTGCTGGGGCCGCCGCCCTGGC

TTTGACCGTGGACCTGCCACCCGCCTCCTCCGAGGCTCGGAACTCGGCC

TTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTAC

CCAGGGCGCCACAGTCTTGGGACTCTTCCGGGTGACCCCCGAAATCCCA

GCCGGACTCCCTTCACCGAGGTCGGAATAA

>Human 4-1BB-L protein sequence (NCBI Reference Sequence: NP_003802.1)

(SEQ ID NO: 16)

MEYASDASLDPEAPWPPAPRARACRVLPWALVAGLLLLLLLAAACAVFL

ACPWAVSGARASPGSAASPRLREGPELSPDDPAGLLDLRQGMFAQLVAQ

-continued

NVLLIDGPLSWYSDPGLAGVSLTGGLSYKEDTKELVVAKAGVYYVFFQL

ELRRVVAGEGSGSVSLALHLQPLRSAAGAAALALTVDLPPASSEARNSA

FGFQGRLLHLSAGQRLGVHLHTEARARHAWQLTQGATVLGLFRVTPEIP

AGLPSPRSE

<OX40-L>

>TNFSF4: TNF superfamily member 4 (aka GP34; CD252; OX40L; TXGP1; CD134L; OX-40L; TNLG2B)

>DNA sequence (NCBI Reference Sequence: NM_003326.4)

(SEQ ID NO: 17)

ATGGAAAGGGTCCAACCCCTGGAAGAGAATGTGGGAAATGCAGCCAGGC

CAAGATTCGAGAGGAACAAGCTATTGCTGGTGGCCTCTGTAATTCAGGG

ACTGGGGCTGCTCCTGTGCTTCACCTACATCTGCCTGCACTTCTCTGCT

CTTCAGGTATCACATCGGTATCCTCGAATTCAAAGTATCAAAGTACAAT

TTACCGAATATAAGAAGGAGAAAGGTTTCATCCTCACTTCCCAAAAGGA

GGATGAAATCATGAAGGTGCAGAACAACTCAGTCATCATCAACTGTGAT

GGGTTTTATCTCATCTCCCTGAAGGGCTACTTCTCCCAGGAAGTCAACA

TTAGCCTTCATTACCAGAAGGATGAGGAGCCCCTCTTCCAACTGAAGAA

GGTCAGGTCTGTCAACTCCTTGATGGTGGCCTCTCTGACTTACAAAGAC

AAAGTCTACTTGAATGTGACCACTGACAATACCTCCCTGGATGACTTCC

ATGTGAATGGCGGAGAACTGATTCTTATCCATCAAAATCCTGGTGAATT

CTGTGTCCTTTGA

>Human OX40-L Protein sequence (NCBI Reference Sequence: NP_003317.1)

(SEQ ID NO: 18)

MERVQPLEENVGNAARPRFERNKLLLVASVIQGLGLLLCFTYICLHFSA

LQVSHRYPRIQSIKVQFTEYKKEKGFILTSQKEDEIMKVQNNSVIINCD

GFYLISLKGYFSQEVNISLHYQKDEEPLFQLKKVRSVNSLMVASLTYKD

KVYLNVTTDNTSLDDFHVNGGELILIHQNPGEFCVL

<GITR-L>

>TNFSF18 TNF superfamily member 18 (aka TL6; AITRL; GITRL; TNLG2A; hGITRL)

>DNA sequence (NCBI Reference Sequence: NM_005092.3)

(SEQ ID NO: 19)

ATGACATTGCATCCTTCACCCATCACTTGTGAATTTTTGTTTTCCACAG

CTCTCATTTCTCCAAAAATGTGTTTGAGCCACTTGGAAAATATGCCTTT

AAGCCATTCAAGAACTCAAGGAGCTCAGAGATCATCCTGGAAGCTGTGG

CTCTTTTGCTCAATAGTTATGTTGCTATTTCTTTGCTCCTTCAGTTGGC

TAATCTTTATTTTTCTCCAATTAGAGACTGCTAAGGAGCCCTGTATGGC

TAAGTTTGGACCATTACCCTCAAAATGGCAAATGGCATCTTCTGAACCT

CCTTGCGTGAATAAGGTGTCTGACTGGAAGCTGGAGATACTTCAGAATG

GCTTATATTTAATTTATGGCCAAGTGGCTCCCAATGCAAACTACAATGA

-continued

TGTAGCTCCTTTTGAGGTGCGGCTGTATAAAAACAAAGACATGATACAA

ACTCTAACAAACAAATCTAAAATCCAAAATGTAGGAGGGACTTATGAAT

TGCATGTTGGGGACACCATAGACTTGATATTCAACTCTGAGCATCAGGT

TCTAAAAAATAATACATACTGGGGTATCATTTTACTAGCAAATCCCCAA

TTCATCTCCTAG

>Human GITR-L Protein sequence (NCBI Reference Sequence: NP_005083.2)

(SEQ ID NO: 20)

MTLHPSPITCEFLFSTALISPKMCLSHLENMPLSHSRTQGAQRSSWKLW

LFCSIVMLLFLCSFSWLIFIFLQLETAKEPCMAKFGPLPSKWQMASSEP

PCVNKVSDWKLEILQNGLYLIYGQVAPNANYNDVAPFEVRLYKNKDMIQ

TLINKSKIQNVGGTYELHVGDTIDLIFNSEHQVLKNNTYWGIILLANPQ

FIS

<CD86>

>CD86 (aka B70; B7-2; B7.2; LAB72; CD28LG2)

>DNA sequences (NCBI Reference Sequence: NM_175862.4)

(SEQ ID NO: 21)

ATGGATCCCCAGTGCACTATGGGACTGAGTAACATTCTCTTTGTGATGG

CCTTCCTGCTCTCTGGTGCTGCTCCTCTGAAGATTCAAGCTTATTTCAA

TGAGACTGCAGACCTGCCATGCCAATTTGCAAACTCTCAAAACCAAAGC

CTGAGTGAGCTAGTAGTATTTTGGCAGGACCAGGAAAACTTGGTTCTGA

ATGAGGTATACTTAGGCAAAGAGAAATTTGACAGTGTTCATTCCAAGTA

TATGGGCCGCACAAGTTTTGATTCGGACAGTTGGACCCTGAGACTTCAC

AATCTTCAGATCAAGGACAAGGGCTTGTATCAATGTATCATCCATCACA

AAAAGCCCACAGGAATGATTCGCATCCACCAGATGAATTCTGAACTGTC

AGTGCTTGCTAACTTCAGTCAACCTGAAATAGTACCAATTTCTAATATA

ACAGAAAATGTGTACATAAATTTGACCTGCTCATCTATACACGGTTACC

CAGAACCTAAGAAGATGAGTGTTTTGCTAAGAACCAAGAATTCAACTAT

CGAGTATGATGGTATTATGCAGAAATCTCAAGATAATGTCACAGAACTG

TACGACGTTTCCATCAGCTTGTCTGTTTCATTCCCTGATGTTACGAGCA

ATATGACCATCTTCTGTATTCTGGAAACTGACAAGACGCGGCTTTTATC

TTCACCTTTCTCTATAGAGCTTGAGGACCCTCAGCCTCCCCCAGACCAC

ATTCCTTGGATTACAGCTGTACTTCCAACAGTTATTATATGTGTGATGG

TTTTCTGTCTAATTCTATGGAAATGGAAGAAGAAGAAGCGGCCTCGCAA

CTCTTATAAATGTGGAACCAACACAATGGAGAGGGAAGAGAGTGAACAG

ACCAAGAAAAGAGAAAAAATCCATATACCTGAAAGATCTGATGAAGCCC

AGCGTGTTTTTAAAAGTTCGAAGACATCTTCATGCGACAAAAGTGATAC

ATGTTTTTAA

>Human CD86 Protein sequence (NCBI Reference Sequence: NP_787058.4)

(SEQ ID NO: 22)

MDPQCTMGLSNILFVMAFLLSGAAPLKIQAYFNETADLPCQFANSQNQS

LSELVVFWQDQENLVLNEVYLGKEKFDSVHSKYMGRTSFDSDSWTLRLH

NLQIKDKGLYQCIIHHKKPTGMIRIHQMNSELSVLANFSQPEIVPISNI

TENVYINLTCSSIHGYPEPKKMSVLLRTKNSTIEYDGIMQKSQDNVTEL

YDVSISLSVSFPDVTSNMTIFCILETDKTRLLSSPFSIELEDPQPPPDH

IPWITAVLPTVIICVMVFCLILWKWKKKKRPRNSYKCGTNTMEREESEQ

TKKREKIHIPERSDEAQRVFKSSKTSSCDKSDTCF

<GM-CSF>

>CSF2: colony stimulating factor 2 (aka CSF; GMCSF)

>DNA sequence (NCBI Reference Sequence: NM 000758.3)

(SEQ ID NO: 23)

ATGTGGCTGCAGAGCCTGCTGCTCTTGGGCACTGTGGCCTGCAGCATCT

CTGCACCCGCCCGCTCGCCCAGCCCCAGCACGCAGCCCTGGGAGCATGT

GAATGCCATCCAGGAGGCCCGGCGTCTCCTGAACCTGAGTAGAGACACT

GCTGCTGAGATGAATGAAACAGTAGAAGTCATCTCAGAAATGTTTGACC

TCCAGGAGCCGACCTGCCTACAGACCCGCCTGGAGCTGTACAAGCAGGG

CCTGCGGGGCAGCCTCACCAAGCTCAAGGGCCCCTTGACCATGATGGCC

AGCCACTACAAGCAGCACTGCCCTCCAACCCCGGAAACTTCCTGTGCAA

CCCAGATTATCACCTTTGAAAGTTTCAAAGAGAACCTGAAGGACTTTCT

GCTTGTCATCCCCTTTGACTGCTGGGAGCCAGTCCAGGAGTGA

>Human GM-CSF protein sequence (NCBI Reference Sequence: NP_000749.2)

(SEQ ID NO: 24)

MWLQSLLLLGTVACSISAPARSPSPSTQPWEHVNAIQEARRLLNLSRDT

AAEMNETVEVISEMFDLQEPTCLQTRLELYKQGLRGSLTKLKGPLTMMA

SHYKQHCPPTPETSCATQIITFESFKENLKDFLLVIPFDCWEPVQE

The foregoing description of specific embodiments is for the purpose of illustration and is not to be construed as restrictive. From the teachings of the present invention, those skilled in the art will recognize that various modifications and changes may be made without departing from the spirit of the invention.

What is claimed is:

1. A method for stimulating an immune response in a human individual against cancer antigens comprised by cancer cells in the individual, the method comprising;

administering to the individual irradiated modified cancer cells comprising modifications consisting of introducing into the cancer cells polynucleotides that result in expression of class II trans-activator (CIITA) comprising the sequence of SEQ ID NO: 14 and 4-1 BB-Ligand comprising the sequence of SEQ ID NO: 16, wherein the immune response is stimulated to one or more antigens expressed by the irradiated modified cancer cells and wherein the cancer cells in the individual are ovarian cancer, colon cancer, or lymphoma cells, and wherein the irradiated modified cancer cells that are administered to the individual are the same type of cancer cells that are present in the individual; the method further comprising determining from a biological sample obtained from the individual development of a cytotoxic anticancer antibody response against the cancer cells in the individual.

2. The method of claim 1, wherein the stimulated immune response also comprises a durable memory anticancer CD8+ T-cell response that is specific for the cancer cells in the individual.

3. The method of claim 1, wherein the modified, irradiated cancer cells are ovarian cancer cells and wherein the cancer cells in the individual are ovarian cancer cells.

4. The method of claim 1, wherein the modified, irradiated cancer cells are colon cancer cells and wherein the cancer cells in the individual are colon cancer cells.

5. The method of claim 1, wherein the modified, irradiated cancer cells are lymphoma cells, and wherein the cancer cells in the individual are lymphoma cells.

* * * * *

SEQUENCE LISTING

```
<160> NUMBER OF SEQ ID NOS: 24

<210> SEQ ID NO 1
<211> LENGTH: 3468
```

<212> TYPE: DNA
<213> ORGANISM: Mus musculus

<400> SEQUENCE: 1
atgaaccact tccaggccat cctggcccaa gtacagacac tgctctccag ccagaagccc 60
aggcaggtgc gggccctcct ggatggcctg ctggaagaag agctgctctc acgggaatac 120
cactgtgcct tgctgcatga gcctgatggt gatgccctgg cccggaagat ttccctgacc 180
ctgctggaga aaggggactt agacttgact ttcttgagct gggtctgcaa cagtctgcag 240
gctcccacgg tagagagggg caccagctac agggaccatg gagaccatag tctgtgtgcc 300
accatggatc tgggatctcc agagggcagc tacctggaac tccttaacag tgatgccgac 360
cccctacatc tctaccacct ctatgaccag atggacctgg ctggggagga ggagatcgaa 420
ctcagctcag agccagacac agataccatc aactgcgacc agttcagcaa gctgttgcag 480
gacatggaac tggatgaaga gacccgggag gcctatgcca acattgcgga actggatcag 540
tacgtgttcc aggataccca gctcgagggc ctgagcaagg acctcttcat agagcacatt 600
ggagcagagg aaggctttgg tgagaacata gagatccctg tagaagcagg acagaagcct 660
cagaagagac gcttcccgga agagcatgct atggactcaa agcacaggaa gctagtgccc 720
acctctagga cctcactgaa ctatttggat ctccccactg ggcacatcca gatcttcacc 780
actctgcccc agggactctg gcaaatctca ggggctggca caggtctctc cagtgtccta 840
atctaccacg gtgagatgcc ccaggtcaac caagtgctcc cttcaagcag cctcagtatc 900
cccagtctcc ccgagtcccc agaccggcct ggctccacca gccccttcac accatctgca 960
gctgacctgc ccagcatgcc cgaacctgcg ctgacctccc gtgtaaatga gacagaggac 1020
acatctccct ccccatgcca agagggtccc gagtcttcca tcaagcttcc aaaatggcca 1080
gaggctgtgg agcgattcca gcactcccta caggacaaat acaaggcatt gccccagagc 1140
ccaaggggtc ctctggtggc cgtggagctg gtacgggcca ggctggaaag aggcagcaac 1200
aagagccagg aaagggagct ggccactccc gactggacag agcgccagct agcccacggt 1260
ggtctggcag aggtacttca ggttgtcagt gactgcaggc gaccaggaga gacacaggtg 1320
gtcgctgtgc tgggcaaggc tggccaggga aagagccact gggccaggac agtgagtcac 1380
acctgggcat gtggccagtt gctacaatat gactttgtct tctatgtccc ctgtcattgc 1440
ttggatcgtc ccggggacac ctaccacctg cgggatctgc tctgtccccc gagcctgcag 1500
ccactggcca tggatgacga ggtccttgat tatatcgtga ggcagccaga ccgtgttctg 1560
ctcatcctag atgctttcga ggagctagag gcccaagatg gcctcctgca cggaccctgt 1620
ggatctctgt ccccagagcc ctgctccctc cgaggactgc tggctgggat cttccagcgg 1680
aagctactgc gaggctgcac actgctcctc acagcccggc cccggggccg cctggctcag 1740
agcctgagca aggcagatgc catctttgag gtgcccagct tctctaccaa gcaggccaag 1800
acttacatga ggcactactt tgagaactca gggacagcgg ggaaccaaga caaggccctg 1860
ggcctcctgg agggccagcc tcttctctgc agctatagtc acagccctgt tgtgtgcagg 1920
gctgtgtgcc agctctccaa ggccctgcta gaacagggca cagaggccca gctaccttgt 1980
acacttacag gactctatgt cagcctgcta ggtcctgcag ctcagaacag tcctcccgga 2040
gccttagtcg agctggccaa gctggcctgg gagctgggac gaagacacca aagcaccttg 2100
caagaaaccc ggttttcatc cgtggaggtg aaaacctggg cagtgaccca aggcttgatg 2160
cagcagaccc tggagaccac ggaggctcaa ctggccttct ccagttttct gctacagtgt 2220

```
ttcctgggtg ctgtgtggct ggcacagtgc aatgaaatca aagacaagga gctgccacag   2280

tacctggcct tgactccgag gaagaagaga ccctatgaca actggctgga gggtgtacca   2340

cgctttctgg ctggattagt tttccagcct cgagcccact gcctgggagc tctggtggag   2400

cctgcagtgg ctgcagtggc ggataggaaa cagaaggttc ttaccaggta cctgaagcgc   2460

ctgaagctgg ggacactccg ggcagggagg ctgctggagc tgctccactg tgcccacgag   2520

acacagcaac ctgggatatg ggagcatgtt gcacaccagc tccctggcca cctctccttc   2580

ctgggcaccc ggctcacacc cccagatgtg tatgtgctgg gcagggcctt ggagacagcc   2640

agccaggact tctccttgga ccttcgtcag actggcgttg agccttctgg actgggaaac   2700

ctcgtgggac tcagctgtgt caccagtttc agggcctcct tgagtgatac aatggcatta   2760

tgggagtccc ttcagcagca gggagaagcc cagctactcc aggcggcaga ggagaagttc   2820

accattgagc catttaaagc caaatcccca aaggatgtgg aagacctgga tcgtctcgtg   2880

cagacccaga ggctgagaaa cccctcagaa gatgcagcca aggatcttcc tgccatccgg   2940

gaccttaaga agctagagtt tgcgttgggc cccatcttgg gcccccaggc tttccccaca   3000

ctggcaaaga tccttccagc cttctcttct ctgcaacacc tggacctgga ctcacttagt   3060

gagaacaaga tcggagacaa gggtgtgtcg aagctctcag ccaccttccc tcagctgaag   3120

gccctggaga cgctcaactt gtcccaaaac aacatcactg atgtgggtgc ctgcaagctt   3180

gcagaagctc tgccagccct agccaagtcc ctcctaaggc tgagcttgta caataactgc   3240

atctgtgaca aaggagccaa gagcctggca caagtacttc cggacatggt gtccctgcgt   3300

gtgatggatg tccagttcaa caagttcacg gctgccggtg cccagcaact ggcctccagc   3360

cttcagaagt gccctcaggt ggaaacactg gcaatgtgga cacccactat cccctttggg   3420

gttcaggaac acctgcagca gctggatgcc aggatcagtc tgagatga                 3468
```

```
<210> SEQ ID NO 2
<211> LENGTH: 1155
<212> TYPE: PRT
<213> ORGANISM: Mus musculus

<400> SEQUENCE: 2

Met Asn His Phe Gln Ala Ile Leu Ala Gln Val Gln Thr Leu Leu Ser
1               5                   10                  15

Ser Gln Lys Pro Arg Gln Val Arg Ala Leu Leu Asp Gly Leu Leu Glu
            20                  25                  30

Glu Glu Leu Leu Ser Arg Glu Tyr His Cys Ala Leu Leu His Glu Pro
        35                  40                  45

Asp Gly Asp Ala Leu Ala Arg Lys Ile Ser Leu Thr Leu Leu Glu Lys
    50                  55                  60

Gly Asp Leu Asp Leu Thr Phe Leu Ser Trp Val Cys Asn Ser Leu Gln
65                  70                  75                  80

Ala Pro Thr Val Glu Arg Gly Thr Ser Tyr Arg Asp His Gly Asp His
                85                  90                  95

Ser Leu Cys Ala Thr Met Asp Leu Gly Ser Pro Glu Gly Ser Tyr Leu
            100                 105                 110

Glu Leu Leu Asn Ser Asp Ala Asp Pro Leu His Leu Tyr His Leu Tyr
        115                 120                 125

Asp Gln Met Asp Leu Ala Gly Glu Glu Glu Ile Glu Leu Ser Ser Glu
    130                 135                 140

Pro Asp Thr Asp Thr Ile Asn Cys Asp Gln Phe Ser Lys Leu Leu Gln
145                 150                 155                 160
```

```
Asp Met Glu Leu Asp Glu Glu Thr Arg Glu Ala Tyr Ala Asn Ile Ala
                165                 170                 175

Glu Leu Asp Gln Tyr Val Phe Gln Asp Thr Gln Leu Glu Gly Leu Ser
            180                 185                 190

Lys Asp Leu Phe Ile Glu His Ile Gly Ala Glu Glu Gly Phe Gly Glu
        195                 200                 205

Asn Ile Glu Ile Pro Val Glu Ala Gly Gln Lys Pro Gln Lys Arg Arg
    210                 215                 220

Phe Pro Glu Glu His Ala Met Asp Ser Lys His Arg Lys Leu Val Pro
225                 230                 235                 240

Thr Ser Arg Thr Ser Leu Asn Tyr Leu Asp Leu Pro Thr Gly His Ile
                245                 250                 255

Gln Ile Phe Thr Thr Leu Pro Gln Gly Leu Trp Gln Ile Ser Gly Ala
            260                 265                 270

Gly Thr Gly Leu Ser Ser Val Leu Ile Tyr His Gly Glu Met Pro Gln
        275                 280                 285

Val Asn Gln Val Leu Pro Ser Ser Ser Leu Ser Ile Pro Ser Leu Pro
    290                 295                 300

Glu Ser Pro Asp Arg Pro Gly Ser Thr Ser Pro Phe Thr Pro Ser Ala
305                 310                 315                 320

Ala Asp Leu Pro Ser Met Pro Glu Pro Ala Leu Thr Ser Arg Val Asn
                325                 330                 335

Glu Thr Glu Asp Thr Ser Pro Ser Pro Cys Gln Glu Gly Pro Glu Ser
            340                 345                 350

Ser Ile Lys Leu Pro Lys Trp Pro Glu Ala Val Glu Arg Phe Gln His
        355                 360                 365

Ser Leu Gln Asp Lys Tyr Lys Ala Leu Pro Gln Ser Pro Arg Gly Pro
    370                 375                 380

Leu Val Ala Val Glu Leu Val Arg Ala Arg Leu Glu Arg Gly Ser Asn
385                 390                 395                 400

Lys Ser Gln Glu Arg Glu Leu Ala Thr Pro Asp Trp Thr Glu Arg Gln
                405                 410                 415

Leu Ala His Gly Gly Leu Ala Glu Val Leu Gln Val Val Ser Asp Cys
            420                 425                 430

Arg Arg Pro Gly Glu Thr Gln Val Val Ala Val Leu Gly Lys Ala Gly
        435                 440                 445

Gln Gly Lys Ser His Trp Ala Arg Thr Val Ser His Thr Trp Ala Cys
    450                 455                 460

Gly Gln Leu Leu Gln Tyr Asp Phe Val Phe Tyr Val Pro Cys His Cys
465                 470                 475                 480

Leu Asp Arg Pro Gly Asp Thr Tyr His Leu Arg Asp Leu Leu Cys Pro
                485                 490                 495

Pro Ser Leu Gln Pro Leu Ala Met Asp Asp Glu Val Leu Asp Tyr Ile
            500                 505                 510

Val Arg Gln Pro Asp Arg Val Leu Leu Ile Leu Asp Ala Phe Glu Glu
        515                 520                 525

Leu Glu Ala Gln Asp Gly Leu Leu His Gly Pro Cys Gly Ser Leu Ser
    530                 535                 540

Pro Glu Pro Cys Ser Leu Arg Gly Leu Leu Ala Gly Ile Phe Gln Arg
545                 550                 555                 560

Lys Leu Leu Arg Gly Cys Thr Leu Leu Leu Thr Ala Arg Pro Arg Gly
                565                 570                 575
```

```
Arg Leu Ala Gln Ser Leu Ser Lys Ala Asp Ala Ile Phe Glu Val Pro
            580                 585                 590

Ser Phe Ser Thr Lys Gln Ala Lys Thr Tyr Met Arg His Tyr Phe Glu
        595                 600                 605

Asn Ser Gly Thr Ala Gly Asn Gln Asp Lys Ala Leu Gly Leu Leu Glu
    610                 615                 620

Gly Gln Pro Leu Leu Cys Ser Tyr Ser His Ser Pro Val Val Cys Arg
625                 630                 635                 640

Ala Val Cys Gln Leu Ser Lys Ala Leu Leu Glu Gln Gly Thr Glu Ala
                645                 650                 655

Gln Leu Pro Cys Thr Leu Thr Gly Leu Tyr Val Ser Leu Leu Gly Pro
            660                 665                 670

Ala Ala Gln Asn Ser Pro Pro Gly Ala Leu Val Glu Leu Ala Lys Leu
        675                 680                 685

Ala Trp Glu Leu Gly Arg Arg His Gln Ser Thr Leu Gln Glu Thr Arg
    690                 695                 700

Phe Ser Ser Val Glu Val Lys Thr Trp Ala Val Thr Gln Gly Leu Met
705                 710                 715                 720

Gln Gln Thr Leu Glu Thr Thr Glu Ala Gln Leu Ala Phe Ser Ser Phe
                725                 730                 735

Leu Leu Gln Cys Phe Leu Gly Ala Val Trp Leu Ala Gln Cys Asn Glu
            740                 745                 750

Ile Lys Asp Lys Glu Leu Pro Gln Tyr Leu Ala Leu Thr Pro Arg Lys
        755                 760                 765

Lys Arg Pro Tyr Asp Asn Trp Leu Glu Gly Val Pro Arg Phe Leu Ala
    770                 775                 780

Gly Leu Val Phe Gln Pro Arg Ala His Cys Leu Gly Ala Leu Val Glu
785                 790                 795                 800

Pro Ala Val Ala Ala Val Ala Asp Arg Lys Gln Lys Val Leu Thr Arg
                805                 810                 815

Tyr Leu Lys Arg Leu Lys Leu Gly Thr Leu Arg Ala Gly Arg Leu Leu
            820                 825                 830

Glu Leu Leu His Cys Ala His Glu Thr Gln Gln Pro Gly Ile Trp Glu
        835                 840                 845

His Val Ala His Gln Leu Pro Gly His Leu Ser Phe Leu Gly Thr Arg
    850                 855                 860

Leu Thr Pro Pro Asp Val Tyr Val Leu Gly Arg Ala Leu Glu Thr Ala
865                 870                 875                 880

Ser Gln Asp Phe Ser Leu Asp Leu Arg Gln Thr Gly Val Glu Pro Ser
                885                 890                 895

Gly Leu Gly Asn Leu Val Gly Leu Ser Cys Val Thr Ser Phe Arg Ala
            900                 905                 910

Ser Leu Ser Asp Thr Met Ala Leu Trp Glu Ser Leu Gln Gln Gln Gly
        915                 920                 925

Glu Ala Gln Leu Leu Gln Ala Ala Glu Glu Lys Phe Thr Ile Glu Pro
    930                 935                 940

Phe Lys Ala Lys Ser Pro Lys Asp Val Glu Asp Leu Asp Arg Leu Val
945                 950                 955                 960

Gln Thr Gln Arg Leu Arg Asn Pro Ser Glu Asp Ala Ala Lys Asp Leu
                965                 970                 975

Pro Ala Ile Arg Asp Leu Lys Lys Leu Glu Phe Ala Leu Gly Pro Ile

            980                 985                 990

Leu Gly Pro Gln Ala Phe Pro Thr  Leu Ala Lys Ile Leu  Pro Ala Phe
```

```
        995                 1000                1005

Ser Ser  Leu Gln His Leu Asp  Leu Asp Ser Leu Ser  Glu Asn Lys
    1010                 1015                1020

Ile Gly  Asp Lys Gly Val Ser  Lys Leu Ser Ala Thr  Phe Pro Gln
    1025                 1030                1035

Leu Lys  Ala Leu Glu Thr Leu  Asn Leu Ser Gln Asn  Asn Ile Thr
    1040                 1045                1050

Asp Val  Gly Ala Cys Lys Leu  Ala Glu Ala Leu Pro  Ala Leu Ala
    1055                 1060                1065

Lys Ser  Leu Leu Arg Leu Ser  Leu Tyr Asn Asn Cys  Ile Cys Asp
    1070                 1075                1080

Lys Gly  Ala Lys Ser Leu Ala  Gln Val Leu Pro Asp  Met Val Ser
    1085                 1090                1095

Leu Arg  Val Met Asp Val Gln  Phe Asn Lys Phe Thr  Ala Ala Gly
    1100                 1105                1110

Ala Gln  Gln Leu Ala Ser Ser  Leu Gln Lys Cys Pro  Gln Val Glu
    1115                 1120                1125

Thr Leu  Ala Met Trp Thr Pro  Thr Ile Pro Phe Gly  Val Gln Glu
    1130                 1135                1140

His Leu  Gln Gln Leu Asp Ala  Arg Ile Ser Leu Arg
    1145                 1150                1155


<210> SEQ ID NO 3
<211> LENGTH: 930
<212> TYPE: DNA
<213> ORGANISM: Mus musculus

<400> SEQUENCE: 3

atggaccagc acacacttga tgtggaggat accgcggatg ccagacatcc agcaggtact     60

tcgtgcccct cggatgcggc gctcctcaga gataccgggc tcctcgcgga cgctgcgctc    120

ctctcagata ctgtgcgccc cacaaatgcc gcgctcccca cggatgctgc ctaccctgcg    180

gttaatgttc gggatcgcga ggccgcgtgg ccgcctgcac tgaacttctg ttcccgccac    240

ccaaagctct atggcctagt cgctttggtt ttgctgcttc tgatcgccgc ctgtgttcct    300

atcttcaccc gcaccgagcc tcggccagcg ctcacaatca ccacctcgcc caacctgggt    360

acccgagaga ataatgcaga ccaggtcacc cctgtttccc acattggctg ccccaacact    420

acacaacagg gctctcctgt gttcgccaag ctactggcta aaaaccaagc atcgttgtgc    480

aatacaactc tgaactggca cagccaagat ggagctggga gctcatacct atctcaaggt    540

ctgaggtacg aagaagacaa aaaggagttg gtggtagaca gtcccgggct ctactacgta    600

tttttggaac tgaagctcag tccaacattc acaaacacag gccacaaggt gcagggctgg    660

gtctctcttg ttttgcaagc aaagcctcag gtagatgact ttgacaactt ggccctgaca    720

gtggaactgt tcccttgctc catggagaac aagttagtgg accgttcctg gagtcaactg    780

ttgctcctga aggctggcca ccgcctcagt gtgggtctga gggcttatct gcatggagcc    840

caggatgcat acagagactg ggagctgtct tatcccaaca ccaccagctt tggactcttt    900

cttgtgaaac ccgacaaccc atgggaatga                                     930


<210> SEQ ID NO 4
<211> LENGTH: 309
<212> TYPE: PRT
<213> ORGANISM: Mus musculus

<400> SEQUENCE: 4
```

```
Met Asp Gln His Thr Leu Asp Val Glu Asp Thr Ala Asp Ala Arg His
1               5                   10                  15

Pro Ala Gly Thr Ser Cys Pro Ser Asp Ala Ala Leu Leu Arg Asp Thr
            20                  25                  30

Gly Leu Leu Ala Asp Ala Ala Leu Leu Ser Asp Thr Val Arg Pro Thr
        35                  40                  45

Asn Ala Ala Leu Pro Thr Asp Ala Ala Tyr Pro Ala Val Asn Val Arg
    50                  55                  60

Asp Arg Glu Ala Ala Trp Pro Pro Ala Leu Asn Phe Cys Ser Arg His
65                  70                  75                  80

Pro Lys Leu Tyr Gly Leu Val Ala Leu Val Leu Leu Leu Leu Ile Ala
                85                  90                  95

Ala Cys Val Pro Ile Phe Thr Arg Thr Glu Pro Arg Pro Ala Leu Thr
            100                 105                 110

Ile Thr Thr Ser Pro Asn Leu Gly Thr Arg Glu Asn Asn Ala Asp Gln
        115                 120                 125

Val Thr Pro Val Ser His Ile Gly Cys Pro Asn Thr Thr Gln Gln Gly
    130                 135                 140

Ser Pro Val Phe Ala Lys Leu Leu Ala Lys Asn Gln Ala Ser Leu Cys
145                 150                 155                 160

Asn Thr Thr Leu Asn Trp His Ser Gln Asp Gly Ala Gly Ser Ser Tyr
                165                 170                 175

Leu Ser Gln Gly Leu Arg Tyr Glu Glu Asp Lys Lys Glu Leu Val Val
            180                 185                 190

Asp Ser Pro Gly Leu Tyr Tyr Val Phe Leu Glu Leu Lys Leu Ser Pro
        195                 200                 205

Thr Phe Thr Asn Thr Gly His Lys Val Gln Gly Trp Val Ser Leu Val
    210                 215                 220

Leu Gln Ala Lys Pro Gln Val Asp Asp Phe Asp Asn Leu Ala Leu Thr
225                 230                 235                 240

Val Glu Leu Phe Pro Cys Ser Met Glu Asn Lys Leu Val Asp Arg Ser
                245                 250                 255

Trp Ser Gln Leu Leu Leu Leu Lys Ala Gly His Arg Leu Ser Val Gly
            260                 265                 270

Leu Arg Ala Tyr Leu His Gly Ala Gln Asp Ala Tyr Arg Asp Trp Glu
        275                 280                 285

Leu Ser Tyr Pro Asn Thr Thr Ser Phe Gly Leu Phe Leu Val Lys Pro
    290                 295                 300

Asp Asn Pro Trp Glu
305
```

<210> SEQ ID NO 5
<211> LENGTH: 597
<212> TYPE: DNA
<213> ORGANISM: Mus musculus

<400> SEQUENCE: 5

```
atggaagggg aaggggttca acccctggat gagaatctgg aaaacggatc aaggccaaga      60

ttcaagtgga agaagacgct aaggctggtg gtctctggga tcaagggagc agggatgctt     120

ctgtgcttca tctatgtctg cctgcaactc tcttcctctc cggcaaagga ccctccaatc     180

caaagactca gaggagcagt taccagatgt gaggatgggc aactattcat cagctcatac     240

aagaatgagt atcaaactat ggaggtgcag aacaattcgg ttgtcatcaa gtgcgatggg     300
```

ctttatatca tctacctgaa gggctccttt ttccaggagg tcaagattga ccttcatttc 360
cgggaggatc ataatcccat ctctattcca atgctgaacg atggtcgaag gattgtcttc 420
actgtggtgg cctctttggc tttcaaagat aaagtttacc tgactgtaaa tgctcctgat 480
actctctgcg aacacctcca gataaatgat ggggagctga ttgttgtcca gctaacgcct 540
ggatactgtg ctcctgaagg atcttaccac agcactgtga accaagtacc actgtga 597

<210> SEQ ID NO 6
<211> LENGTH: 198
<212> TYPE: PRT
<213> ORGANISM: Mus musculus

<400> SEQUENCE: 6

```
Met Glu Gly Glu Gly Val Gln Pro Leu Asp Glu Asn Leu Glu Asn Gly
1               5                   10                  15

Ser Arg Pro Arg Phe Lys Trp Lys Lys Thr Leu Arg Leu Val Val Ser
            20                  25                  30

Gly Ile Lys Gly Ala Gly Met Leu Leu Cys Phe Ile Tyr Val Cys Leu
        35                  40                  45

Gln Leu Ser Ser Ser Pro Ala Lys Asp Pro Pro Ile Gln Arg Leu Arg
    50                  55                  60

Gly Ala Val Thr Arg Cys Glu Asp Gly Gln Leu Phe Ile Ser Ser Tyr
65                  70                  75                  80

Lys Asn Glu Tyr Gln Thr Met Glu Val Gln Asn Asn Ser Val Val Ile
                85                  90                  95

Lys Cys Asp Gly Leu Tyr Ile Ile Tyr Leu Lys Gly Ser Phe Phe Gln
            100                 105                 110

Glu Val Lys Ile Asp Leu His Phe Arg Glu Asp His Asn Pro Ile Ser
        115                 120                 125

Ile Pro Met Leu Asn Asp Gly Arg Arg Ile Val Phe Thr Val Val Ala
    130                 135                 140

Ser Leu Ala Phe Lys Asp Lys Val Tyr Leu Thr Val Asn Ala Pro Asp
145                 150                 155                 160

Thr Leu Cys Glu His Leu Gln Ile Asn Asp Gly Glu Leu Ile Val Val
                165                 170                 175

Gln Leu Thr Pro Gly Tyr Cys Ala Pro Glu Gly Ser Tyr His Ser Thr
            180                 185                 190

Val Asn Gln Val Pro Leu
        195
```

<210> SEQ ID NO 7
<211> LENGTH: 522
<212> TYPE: DNA
<213> ORGANISM: Mus musculus

<400> SEQUENCE: 7
atggaggaaa tgcctttgag agaatcaagt cctcaaaggg cagagaggtg caagaagtca 60
tggctcttgt gcatagtggc tctgttactg atgttgctct gttctttggg tacactgatc 120
tatacttcac tcaagccaac tgccatcgag tcctgcatgg ttaagtttga actatcatcc 180
tcaaaatggc acatgacatc tcccaaacct cactgtgtga atacgacatc tgatgggaag 240
ctgaagatac tgcagagtgg cacatattta atctacggcc aagtgattcc tgtggataag 300
aaatacataa aagacaatgc ccccttcgta gtacagatat ataaaaagaa tgatgtccta 360
caaactctaa tgaatgattt tcaaatcttg cctataggag ggtttatgaa actgcatgct 420

```
ggagataaca tatatctgaa gttcaactct aaagaccata ttcagaaaac taacacatac    480

tgggggatca tcttaatgcc tgatctacca ttcatctctt ag                       522


<210> SEQ ID NO 8
<211> LENGTH: 173
<212> TYPE: PRT
<213> ORGANISM: Mus musculus

<400> SEQUENCE: 8

Met Glu Glu Met Pro Leu Arg Glu Ser Ser Pro Gln Arg Ala Glu Arg
1               5                   10                  15

Cys Lys Lys Ser Trp Leu Leu Cys Ile Val Ala Leu Leu Leu Met Leu
            20                  25                  30

Leu Cys Ser Leu Gly Thr Leu Ile Tyr Thr Ser Leu Lys Pro Thr Ala
        35                  40                  45

Ile Glu Ser Cys Met Val Lys Phe Glu Leu Ser Ser Ser Lys Trp His
    50                  55                  60

Met Thr Ser Pro Lys Pro His Cys Val Asn Thr Thr Ser Asp Gly Lys
65                  70                  75                  80

Leu Lys Ile Leu Gln Ser Gly Thr Tyr Leu Ile Tyr Gly Gln Val Ile
                85                  90                  95

Pro Val Asp Lys Lys Tyr Ile Lys Asp Asn Ala Pro Phe Val Val Gln
            100                 105                 110

Ile Tyr Lys Lys Asn Asp Val Leu Gln Thr Leu Met Asn Asp Phe Gln
        115                 120                 125

Ile Leu Pro Ile Gly Gly Val Tyr Glu Leu His Ala Gly Asp Asn Ile
    130                 135                 140

Tyr Leu Lys Phe Asn Ser Lys Asp His Ile Gln Lys Thr Asn Thr Tyr
145                 150                 155                 160

Trp Gly Ile Ile Leu Met Pro Asp Leu Pro Phe Ile Ser
                165                 170


<210> SEQ ID NO 9
<211> LENGTH: 921
<212> TYPE: DNA
<213> ORGANISM: Mus musculus

<400> SEQUENCE: 9

atggcttgca attgtcagtt gatgcaggat acaccactcc tcaagtttcc atgtccaagg     60

ctcattcttc tctttgtgct gctgattcgt ctttcacaag tgtcttcaga tgttgatgaa    120

caactgtcca agtcagtgaa agataaggta ttgctgcctt gccgttacaa ctctcctcat    180

gaagatgagt ctgaagaccg aatctactgg caaaaacatg acaaagtggt gctgtctgtc    240

attgctggga aactaaaagt gtggcccgag tataagaacc ggactttata tgacaacact    300

acctactctc ttatcatcct gggcctggtc ctttcagacc ggggcacata cagctgtgtc    360

gttcaaaaga aggaaagagg aacgtatgaa gttaaacact tggctttagt aaagttgtcc    420

atcaaagctg acttctctac ccccaacata actgagtctg gaaacccatc tgcagacact    480

aaaaggatta cctgctttgc ttccgggggt ttcccaaagc ctcgcttctc ttggttggaa    540

aatggaagag aattacctgg catcaatacg acaatttccc aggatcctga atctgaattg    600

tacaccatta gtagccaact agatttcaat acgactcgca accacaccat taagtgtctc    660

attaaatatg gagatgctca cgtgtcagag gacttcacct gggaaaaacc cccagaagac    720

cctcctgata gcaagaacac acttgtgctc tttggggcag gattcggcgc agtaataaca    780
```

-continued

```
gtcgtcgtca tcgttgtcat catcaaatgc ttctgtaagc acagaagctg tttcagaaga    840

aatgaggcaa gcagagaaac aaacaacagc cttaccttcg ggcctgaaga agcattagct    900

gaacagaccg tcttccttta g                                              921


<210> SEQ ID NO 10
<211> LENGTH: 306
<212> TYPE: PRT
<213> ORGANISM: Mus musculus

<400> SEQUENCE: 10

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Trp Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Lys Pro Pro Glu Asp
225                 230                 235                 240

Pro Pro Asp Ser Lys Asn Thr Leu Val Leu Phe Gly Ala Gly Phe Gly
                245                 250                 255

Ala Val Ile Thr Val Val Val Ile Val Val Ile Ile Lys Cys Phe Cys
            260                 265                 270

Lys His Arg Ser Cys Phe Arg Arg Asn Glu Ala Ser Arg Glu Thr Asn
        275                 280                 285

Asn Ser Leu Thr Phe Gly Pro Glu Glu Ala Leu Ala Glu Gln Thr Val
    290                 295                 300

Phe Leu
305


<210> SEQ ID NO 11
<211> LENGTH: 426
<212> TYPE: DNA
<213> ORGANISM: Mus musculus
```

<400> SEQUENCE: 11
atgtggctgc agaatttact tttcctgggc attgtggtct acagcctctc agcacccacc 60
cgctcaccca tcactgtcac ccggccttgg aagcatgtag aggccatcaa agaagccctg 120
aacctcctgg atgacatgcc tgtcacgttg aatgaagagg tagaagtcgt ctctaacgag 180
ttctccttca agaagctaac atgtgtgcag acccgcctga agatattcga gcagggtcta 240
cggggcaatt tcaccaaact caagggcgcc ttgaacatga cagccagcta ctaccagaca 300
tactgccccc caactccgga aacggactgt gaaacacaag ttaccaccta tgcggatttc 360
atagacagcc ttaaaacctt tctgactgat atcccctttg aatgcaaaaa accaggccaa 420
aaatga 426

<210> SEQ ID NO 12
<211> LENGTH: 141
<212> TYPE: PRT
<213> ORGANISM: Mus musculus

<400> SEQUENCE: 12

Met Trp Leu Gln Asn Leu Leu Phe Leu Gly Ile Val Val Tyr Ser Leu
1 5 10 15

Ser Ala Pro Thr Arg Ser Pro Ile Thr Val Thr Arg Pro Trp Lys His
20 25 30

Val Glu Ala Ile Lys Glu Ala Leu Asn Leu Leu Asp Asp Met Pro Val
35 40 45

Thr Leu Asn Glu Glu Val Glu Val Val Ser Asn Glu Phe Ser Phe Lys
50 55 60

Lys Leu Thr Cys Val Gln Thr Arg Leu Lys Ile Phe Glu Gln Gly Leu
65 70 75 80

Arg Gly Asn Phe Thr Lys Leu Lys Gly Ala Leu Asn Met Thr Ala Ser
85 90 95

Tyr Tyr Gln Thr Tyr Cys Pro Pro Thr Pro Glu Thr Asp Cys Glu Thr
100 105 110

Gln Val Thr Thr Tyr Ala Asp Phe Ile Asp Ser Leu Lys Thr Phe Leu
115 120 125

Thr Asp Ile Pro Phe Glu Cys Lys Lys Pro Gly Gln Lys
130 135 140

<210> SEQ ID NO 13
<211> LENGTH: 3396
<212> TYPE: DNA
<213> ORGANISM: Homo sapiens

<400> SEQUENCE: 13
atgcgttgcc tggctccacg ccctgctggg tcctacctgt cagagcccca aggcagctca 60
cagtgtgcca ccatggagtt ggggccccta gaaggtggct acctggagct tcttaacagc 120
gatgctgacc ccctgtgcct ctaccacttc tatgaccaga tggacctggc tggagaagaa 180
gagattgagc tctactcaga acccgacaca gacaccatca actgcgacca gttcagcagg 240
ctgttgtgtg acatggaagg tgatgaagag accagggagg cttatgccaa tatcgcggaa 300
ctggaccagt atgtcttcca ggactcccag ctggagggcc tgagcaagga cattttcata 360
gagcacatag gaccagatga agtgatcggt gagagtatgg agatgccagc agaagttggg 420
cagaaaagtc agaaaagacc cttcccagag gagcttccgg cagacctgaa gcactggaag 480
ccagctgagc cccccactgt ggtgactggc agtctcctag tgggaccagt gagcgactgc 540

-continued

```
tccaccctgc cctgcctgcc actgcctgcg ctgttcaacc aggagccagc ctccggccag    600
atgcgcctgg agaaaaccga ccagattccc atgcctttct ccagttcctc gttgagctgc    660
ctgaatctcc ctgagggacc catccagttt gtccccacca tctccactct gccccatggg    720
ctctggcaaa tctctgaggc tggaacaggg gtctccagta tattcatcta ccatggtgag    780
gtgccccagg ccagccaagt accccctccc agtggattca ctgtccacgg cctcccaaca    840
tctccagacc ggccaggctc caccagcccc ttcgctccat cagccactga cctgcccagc    900
atgcctgaac ctgccctgac ctcccgagca aacatgacag agcacaagac gtcccccacc    960
caatgcccgg cagctggaga ggtctccaac aagcttccaa aatggcctga gccggtggag   1020
cagttctacc gctcactgca ggacacgtat ggtgccgagc ccgcaggccc ggatggcatc   1080
ctagtggagg tggatctggt gcaggccagg ctggagagga gcagcagcaa gagcctggag   1140
cgggaactgg ccaccccgga ctgggcagaa cggcagctgg cccaaggagg cctggctgag   1200
gtgctgttgg ctgccaagga gcaccggcgg ccgcgtgaga cacgagtgat tgctgtgctg   1260
ggcaaagctg gtcagggcaa gagctattgg gctggggcag tgagccgggc ctgggcttgt   1320
ggccggcttc cccagtacga ctttgtcttc tctgtcccct gccattgctt gaaccgtccg   1380
ggggatgcct atggcctgca ggatctgctc ttctccctgg gcccacagcc actcgtggcg   1440
gccgatgagg ttttcagcca catcttgaag agacctgacc gcgttctgct catcctagac   1500
ggcttcgagg agctggaagc gcaagatggc ttcctgcaca gcacgtgcgg accggcaccg   1560
gcggagccct gctccctccg gggctgctg gccggccttt tccagaagaa gctgctccga   1620
ggttgcaccc tcctcctcac agcccggccc cggggccgcc tggtccagag cctgagcaag   1680
gccgacgccc tatttgagct gtccggcttc tccatggagc aggcccaggc atacgtgatg   1740
cgctactttg agagctcagg gatgacagag caccaagaca gagccctgac gctcctccgg   1800
gaccggccac ttcttctcag tcacagccac agccctactt tgtgccgggc agtgtgccag   1860
ctctcagagg ccctgctgga gcttggggag gacgccaagc tgccctccac gctcacggga   1920
ctctatgtcg gcctgctggg ccgtgcagcc ctcgacagcc cccccggggc cctggcagag   1980
ctggccaagc tggcctggga gctgggccgc agacatcaaa gtaccctaca ggaggaccag   2040
ttcccatccg cagacgtgag gacctgggcg atggccaaag gcttagtcca acacccaccg   2100
cgggccgcag agtccgagct ggccttcccc agcttcctcc tgcaatgctt cctgggggcc   2160
ctgtggctgg ctctgagtgg cgaaatcaag gacaaggagc tcccgcagta cctagcattg   2220
accccaagga agaagaggcc ctatgacaac tggctggagg gcgtgccacg ctttctggct   2280
gggctgatct tccagcctcc cgcccgctgc ctgggagccc tactcgggcc atcggcggct   2340
gcctcggtgg acaggaagca gaaggtgctt gcgaggtacc tgaagcggct gcagccgggg   2400
acactgcggg cgcggcagct gctggagctg ctgcactgcg cccacgaggc cgaggaggct   2460
ggaatttggc agcacgtggt acaggagctc cccggccgcc tctcttttct gggcacccgc   2520
ctcacgcctc ctgatgcaca tgtactgggc aaggccttgg aggcggcggg ccaagacttc   2580
tccctggacc tccgcagcac tggcatttgc ccctctggat tggggagcct cgtgggactc   2640
agctgtgtca cccgtttcag ggctgccttg agcgacacgg tggcgctgtg ggagtccctg   2700
cagcagcatg gggagaccaa gctacttcag gcagcagagg agaagttcac catcgagcct   2760
ttcaaagcca agtccctgaa ggatgtggaa gacctgggaa agcttgtgca gactcagagg   2820
acgagaagtt cctcggaaga cacagctggg gagctccctg ctgttcggga cctaaagaaa   2880
```

-continued

```
ctggagtttg cgctgggccc tgtctcaggc ccccaggctt tccccaaact ggtgcggatc   2940

ctcacggcct tttcctccct gcagcatctg gacctggatg cgctgagtga gaacaagatc   3000

ggggacgagg gtgtctcgca gctctcagcc accttccccc agctgaagtc cttggaaacc   3060

ctcaatctgt cccagaacaa catcactgac ctgggtgcct acaaactcgc cgaggccctg   3120

ccttcgctcg ctgcatccct gctcaggcta agcttgtaca ataactgcat ctgcgacgtg   3180

ggagccgaga gcttggctcg tgtgcttccg gacatggtgt ccctccgggt gatggacgtc   3240

cagtacaaca agttcacggc tgccggggcc cagcagctcg ctgccagcct tcggaggtgt   3300

cctcatgtgg agacgctggc gatgtggacg cccaccatcc cattcagtgt ccaggaacac   3360

ctgcaacaac aggattcacg gatcagcctg agatga                             3396
```

```
<210> SEQ ID NO 14
<211> LENGTH: 1131
<212> TYPE: PRT
<213> ORGANISM: Homo sapiens

<400> SEQUENCE: 14

Met Arg Cys Leu Ala Pro Arg Pro Ala Gly Ser Tyr Leu Ser Glu Pro
1               5                   10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Ile Glu His Ile Gly Pro Asp Glu Val
        115                 120                 125

Ile Gly Glu Ser Met Glu Met Pro Ala Glu Val Gly Gln Lys Ser Gln
    130                 135                 140

Lys Arg Pro Phe Pro Glu Glu Leu Pro Ala Asp Leu Lys His Trp Lys
145                 150                 155                 160

Pro Ala Glu Pro Pro Thr Val Val Thr Gly Ser Leu Leu Val Gly Pro
                165                 170                 175

Val Ser Asp Cys Ser Thr Leu Pro Cys Leu Pro Leu Pro Ala Leu Phe
            180                 185                 190

Asn Gln Glu Pro Ala Ser Gly Gln Met Arg Leu Glu Lys Thr Asp Gln
        195                 200                 205

Ile Pro Met Pro Phe Ser Ser Ser Ser Leu Ser Cys Leu Asn Leu Pro
    210                 215                 220

Glu Gly Pro Ile Gln Phe Val Pro Thr Ile Ser Thr Leu Pro His Gly
225                 230                 235                 240

Leu Trp Gln Ile Ser Glu Ala Gly Thr Gly Val Ser Ser Ile Phe Ile
                245                 250                 255

Tyr His Gly Glu Val Pro Gln Ala Ser Gln Val Pro Pro Pro Ser Gly
            260                 265                 270

Phe Thr Val His Gly Leu Pro Thr Ser Pro Asp Arg Pro Gly Ser Thr
        275                 280                 285
```

```
Ser Pro Phe Ala Pro Ser Ala Thr Asp Leu Pro Ser Met Pro Glu Pro
    290                 295                 300

Ala Leu Thr Ser Arg Ala Asn Met Thr Glu His Lys Thr Ser Pro Thr
305                 310                 315                 320

Gln Cys Pro Ala Ala Gly Glu Val Ser Asn Lys Leu Pro Lys Trp Pro
                325                 330                 335

Glu Pro Val Glu Gln Phe Tyr Arg Ser Leu Gln Asp Thr Tyr Gly Ala
            340                 345                 350

Glu Pro Ala Gly Pro Asp Gly Ile Leu Val Glu Val Asp Leu Val Gln
        355                 360                 365

Ala Arg Leu Glu Arg Ser Ser Ser Lys Ser Leu Glu Arg Glu Leu Ala
    370                 375                 380

Thr Pro Asp Trp Ala Glu Arg Gln Leu Ala Gln Gly Gly Leu Ala Glu
385                 390                 395                 400

Val Leu Leu Ala Ala Lys Glu His Arg Arg Pro Arg Glu Thr Arg Val
                405                 410                 415

Ile Ala Val Leu Gly Lys Ala Gly Gln Gly Lys Ser Tyr Trp Ala Gly
            420                 425                 430

Ala Val Ser Arg Ala Trp Ala Cys Gly Arg Leu Pro Gln Tyr Asp Phe
        435                 440                 445

Val Phe Ser Val Pro Cys His Cys Leu Asn Arg Pro Gly Asp Ala Tyr
    450                 455                 460

Gly Leu Gln Asp Leu Leu Phe Ser Leu Gly Pro Gln Pro Leu Val Ala
465                 470                 475                 480

Ala Asp Glu Val Phe Ser His Ile Leu Lys Arg Pro Asp Arg Val Leu
                485                 490                 495

Leu Ile Leu Asp Gly Phe Glu Glu Leu Glu Ala Gln Asp Gly Phe Leu
            500                 505                 510

His Ser Thr Cys Gly Pro Ala Pro Ala Glu Pro Cys Ser Leu Arg Gly
        515                 520                 525

Leu Leu Ala Gly Leu Phe Gln Lys Lys Leu Leu Arg Gly Cys Thr Leu
    530                 535                 540

Leu Leu Thr Ala Arg Pro Arg Gly Arg Leu Val Gln Ser Leu Ser Lys
545                 550                 555                 560

Ala Asp Ala Leu Phe Glu Leu Ser Gly Phe Ser Met Glu Gln Ala Gln
                565                 570                 575

Ala Tyr Val Met Arg Tyr Phe Glu Ser Ser Gly Met Thr Glu His Gln
            580                 585                 590

Asp Arg Ala Leu Thr Leu Leu Arg Asp Arg Pro Leu Leu Leu Ser His
        595                 600                 605

Ser His Ser Pro Thr Leu Cys Arg Ala Val Cys Gln Leu Ser Glu Ala
    610                 615                 620

Leu Leu Glu Leu Gly Glu Asp Ala Lys Leu Pro Ser Thr Leu Thr Gly
625                 630                 635                 640

Leu Tyr Val Gly Leu Leu Gly Arg Ala Ala Leu Asp Ser Pro Pro Gly
                645                 650                 655

Ala Leu Ala Glu Leu Ala Lys Leu Ala Trp Glu Leu Gly Arg Arg His
            660                 665                 670

Gln Ser Thr Leu Gln Glu Asp Gln Phe Pro Ser Ala Asp Val Arg Thr
        675                 680                 685

Trp Ala Met Ala Lys Gly Leu Val Gln His Pro Pro Arg Ala Ala Glu
    690                 695                 700
```

-continued

```
Ser Glu Leu Ala Phe Pro Ser Phe Leu Leu Gln Cys Phe Leu Gly Ala
705                 710                 715                 720

Leu Trp Leu Ala Leu Ser Gly Glu Ile Lys Asp Lys Glu Leu Pro Gln
                725                 730                 735

Tyr Leu Ala Leu Thr Pro Arg Lys Lys Arg Pro Tyr Asp Asn Trp Leu
            740                 745                 750

Glu Gly Val Pro Arg Phe Leu Ala Gly Leu Ile Phe Gln Pro Pro Ala
        755                 760                 765

Arg Cys Leu Gly Ala Leu Leu Gly Pro Ser Ala Ala Ala Ser Val Asp
    770                 775                 780

Arg Lys Gln Lys Val Leu Ala Arg Tyr Leu Lys Arg Leu Gln Pro Gly
785                 790                 795                 800

Thr Leu Arg Ala Arg Gln Leu Leu Glu Leu Leu His Cys Ala His Glu
                805                 810                 815

Ala Glu Glu Ala Gly Ile Trp Gln His Val Val Gln Glu Leu Pro Gly
            820                 825                 830

Arg Leu Ser Phe Leu Gly Thr Arg Leu Thr Pro Pro Asp Ala His Val
        835                 840                 845

Leu Gly Lys Ala Leu Glu Ala Ala Gly Gln Asp Phe Ser Leu Asp Leu
    850                 855                 860

Arg Ser Thr Gly Ile Cys Pro Ser Gly Leu Gly Ser Leu Val Gly Leu
865                 870                 875                 880

Ser Cys Val Thr Arg Phe Arg Ala Ala Leu Ser Asp Thr Val Ala Leu
                885                 890                 895

Trp Glu Ser Leu Gln Gln His Gly Glu Thr Lys Leu Leu Gln Ala Ala
            900                 905                 910

Glu Glu Lys Phe Thr Ile Glu Pro Phe Lys Ala Lys Ser Leu Lys Asp
        915                 920                 925

Val Glu Asp Leu Gly Lys Leu Val Gln Thr Gln Arg Thr Arg Ser Ser
    930                 935                 940

Ser Glu Asp Thr Ala Gly Glu Leu Pro Ala Val Arg Asp Leu Lys Lys
945                 950                 955                 960

Leu Glu Phe Ala Leu Gly Pro Val Ser Gly Pro Gln Ala Phe Pro Lys
                965                 970                 975

Leu Val Arg Ile Leu Thr Ala Phe Ser Ser Leu Gln His Leu Asp Leu
            980                 985                 990

Asp Ala Leu Ser Glu Asn Lys Ile  Gly Asp Glu Gly Val  Ser Gln Leu
        995                 1000                1005

Ser Ala  Thr Phe Pro Gln Leu  Lys Ser Leu Glu Thr  Leu Asn Leu
    1010                1015                1020

Ser Gln  Asn Asn Ile Thr Asp  Leu Gly Ala Tyr Lys  Leu Ala Glu
    1025                1030                1035

Ala Leu  Pro Ser Leu Ala Ala  Ser Leu Leu Arg Leu  Ser Leu Tyr
    1040                1045                1050

Asn Asn  Cys Ile Cys Asp Val  Gly Ala Glu Ser Leu  Ala Arg Val
    1055                1060                1065

Leu Pro  Asp Met Val Ser Leu  Arg Val Met Asp Val  Gln Tyr Asn
    1070                1075                1080

Lys Phe  Thr Ala Ala Gly Ala  Gln Gln Leu Ala Ala  Ser Leu Arg
    1085                1090                1095

Arg Cys  Pro His Val Glu Thr  Leu Ala Met Trp Thr  Pro Thr Ile
    1100                1105                1110

Pro Phe  Ser Val Gln Glu His  Leu Gln Gln Gln Asp  Ser Arg Ile
```

-continued

```
    1115                1120                1125

Ser Leu  Arg
    1130


<210> SEQ ID NO 15
<211> LENGTH: 765
<212> TYPE: DNA
<213> ORGANISM: Homo sapiens

<400> SEQUENCE: 15

atggaatacg cctctgacgc ttcactggac cccgaagccc cgtggcctcc cgcgccccgc      60

gctcgcgcct gccgcgtact gccttgggcc ctggtcgcgg ggctgctgct gctgctgctg     120

ctcgctgccg cctgcgccgt cttcctcgcc tgcccctggg ccgtgtccgg ggctcgcgcc     180

tcgcccggct ccgcggccag cccgagactc cgcgagggtc ccgagctttc gcccgacgat     240

cccgccggcc tcttggacct gcggcagggc atgtttgcgc agctggtggc ccaaaatgtt     300

ctgctgatcg atgggcccct gagctggtac agtgacccag gcctggcagg cgtgtccctg     360

acgggggggcc tgagctacaa agaggacacg aaggagctgg tggtggccaa ggctggagtc    420

tactatgtct tctttcaact agagctgcgg cgcgtggtgg ccggcgaggg ctcaggctcc     480

gtttcacttg cgctgcacct gcagccactg cgctctgctg ctggggccgc cgccctggct     540

ttgaccgtgg acctgccacc cgcctcctcc gaggctcgga actcggcctt cggtttccag     600

ggccgcttgc tgcacctgag tgccggccag cgcctgggcg tccatcttca cactgaggcc     660

agggcacgcc atgcctggca gcttacccag ggcgccacag tcttgggact cttccgggtg     720

acccccgaaa tcccagccgg actcccttca ccgaggtcgg aataa                     765


<210> SEQ ID NO 16
<211> LENGTH: 254
<212> TYPE: PRT
<213> ORGANISM: Homo sapiens

<400> SEQUENCE: 16

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175
```

Ala Ala Leu Ala Leu Thr Val Asp Leu Pro Pro Ala Ser Ser Glu Ala
180 185 190

Arg Asn Ser Ala Phe Gly Phe Gln Gly Arg Leu Leu His Leu Ser Ala
195 200 205

Gly Gln Arg Leu Gly Val His Leu His Thr Glu Ala Arg Ala Arg His
210 215 220

Ala Trp Gln Leu Thr Gln Gly Ala Thr Val Leu Gly Leu Phe Arg Val
225 230 235 240

Thr Pro Glu Ile Pro Ala Gly Leu Pro Ser Pro Arg Ser Glu
245 250

<210> SEQ ID NO 17
<211> LENGTH: 552
<212> TYPE: DNA
<213> ORGANISM: Homo sapiens

<400> SEQUENCE: 17
atggaaaggg tccaacccct ggaagagaat gtgggaaatg cagccaggcc aagattcgag 60
aggaacaagc tattgctggt ggcctctgta attcagggac tggggctgct cctgtgcttc 120
acctacatct gcctgcactt ctctgctctt caggtatcac atcggtatcc tcgaattcaa 180
agtatcaaag tacaatttac cgaatataag aaggagaaag gtttcatcct cacttcccaa 240
aaggaggatg aaatcatgaa ggtgcagaac aactcagtca tcatcaactg tgatgggttt 300
tatctcatct ccctgaaggg ctacttctcc caggaagtca acattagcct tcattaccag 360
aaggatgagg agcccctctt ccaactgaag aaggtcaggt ctgtcaactc cttgatggtg 420
gcctctctga cttacaaaga caaagtctac ttgaatgtga ccactgacaa tacctccctg 480
gatgacttcc atgtgaatgg cggagaactg attcttatcc atcaaaatcc tggtgaattc 540
tgtgtccttt ga 552

<210> SEQ ID NO 18
<211> LENGTH: 183
<212> TYPE: PRT
<213> ORGANISM: Homo sapiens

<400> SEQUENCE: 18

Met Glu Arg Val Gln Pro Leu Glu Glu Asn Val Gly Asn Ala Ala Arg
1 5 10 15

Pro Arg Phe Glu Arg Asn Lys Leu Leu Leu Val Ala Ser Val Ile Gln
20 25 30

Gly Leu Gly Leu Leu Leu Cys Phe Thr Tyr Ile Cys Leu His Phe Ser
35 40 45

Ala Leu Gln Val Ser His Arg Tyr Pro Arg Ile Gln Ser Ile Lys Val
50 55 60

Gln Phe Thr Glu Tyr Lys Lys Glu Lys Gly Phe Ile Leu Thr Ser Gln
65 70 75 80

Lys Glu Asp Glu Ile Met Lys Val Gln Asn Asn Ser Val Ile Ile Asn
85 90 95

Cys Asp Gly Phe Tyr Leu Ile Ser Leu Lys Gly Tyr Phe Ser Gln Glu
100 105 110

Val Asn Ile Ser Leu His Tyr Gln Lys Asp Glu Glu Pro Leu Phe Gln
115 120 125

Leu Lys Lys Val Arg Ser Val Asn Ser Leu Met Val Ala Ser Leu Thr
130 135 140

-continued

```
Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180


<210> SEQ ID NO 19
<211> LENGTH: 600
<212> TYPE: DNA
<213> ORGANISM: Homo sapiens

<400> SEQUENCE: 19

atgacattgc atccttcacc catcacttgt gaatttttgt tttccacagc tctcatttct     60

ccaaaaatgt gtttgagcca cttggaaaat atgcctttaa gccattcaag aactcaagga    120

gctcagagat catcctggaa gctgtggctc ttttgctcaa tagttatgtt gctatttctt    180

tgctccttca gttggctaat ctttattttt ctccaattag agactgctaa ggagccctgt    240

atggctaagt ttggaccatt accctcaaaa tggcaaatgg catcttctga acctccttgc    300

gtgaataagg tgtctgactg gaagctggag atacttcaga atggcttata tttaatttat    360

ggccaagtgg ctcccaatgc aaactacaat gatgtagctc cttttgaggt gcggctgtat    420

aaaaacaaag acatgataca aactctaaca aacaaatcta aaatccaaaa tgtaggaggg    480

acttatgaat tgcatgttgg ggacaccata gacttgatat tcaactctga gcatcaggtt    540

ctaaaaaata atacatactg ggtatcatt ttactagcaa atccccaatt catctcctag    600


<210> SEQ ID NO 20
<211> LENGTH: 199
<212> TYPE: PRT
<213> ORGANISM: Homo sapiens

<400> SEQUENCE: 20

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
    50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
    130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
```

180 185 190

Ala Asn Pro Gln Phe Ile Ser
195

<210> SEQ ID NO 21
<211> LENGTH: 990
<212> TYPE: DNA
<213> ORGANISM: Homo sapiens

<400> SEQUENCE: 21
atggatcccc agtgcactat gggactgagt aacattctct ttgtgatggc cttcctgctc 60
tctggtgctg ctcctctgaa gattcaagct tatttcaatg agactgcaga cctgccatgc 120
caatttgcaa actctcaaaa ccaaagcctg agtgagctag tagtattttg gcaggaccag 180
gaaaacttgg ttctgaatga ggtatactta ggcaaagaga aatttgacag tgttcattcc 240
aagtatatgg gccgcacaag ttttgattcg gacagttgga ccctgagact tcacaatctt 300
cagatcaagg acaagggctt gtatcaatgt atcatccatc acaaaaagcc cacaggaatg 360
attcgcatcc accagatgaa ttctgaactg tcagtgcttg ctaacttcag tcaacctgaa 420
atagtaccaa tttctaatat aacagaaaat gtgtacataa atttgacctg ctcatctata 480
cacggttacc cagaacctaa gaagatgagt gttttgctaa gaaccaagaa ttcaactatc 540
gagtatgatg gtattatgca gaaatctcaa gataatgtca cagaactgta cgacgtttcc 600
atcagcttgt ctgtttcatt ccctgatgtt acgagcaata tgaccatctt ctgtattctg 660
gaaactgaca agacgcggct tttatcttca cctttctcta tagagcttga ggaccctcag 720
cctcccccag accacattcc ttggattaca gctgtacttc caacagttat tatatgtgtg 780
atggttttct gtctaattct atggaaatgg aagaagaaga agcggcctcg caactcttat 840
aaatgtggaa ccaacacaat ggagagggaa gagagtgaac agaccaagaa aagagaaaaa 900
atccatatac ctgaaagatc tgatgaagcc cagcgtgttt ttaaaagttc gaagacatct 960
tcatgcgaca aaagtgatac atgtttttaa 990

<210> SEQ ID NO 22
<211> LENGTH: 329
<212> TYPE: PRT
<213> ORGANISM: Homo sapiens

<400> SEQUENCE: 22

Met Asp Pro Gln Cys Thr Met Gly Leu Ser Asn Ile Leu Phe Val Met
1 5 10 15

Ala Phe Leu Leu Ser Gly Ala Ala Pro Leu Lys Ile Gln Ala Tyr Phe
20 25 30

Asn Glu Thr Ala Asp Leu Pro Cys Gln Phe Ala Asn Ser Gln Asn Gln
35 40 45

Ser Leu Ser Glu Leu Val Val Phe Trp Gln Asp Gln Glu Asn Leu Val
50 55 60

Leu Asn Glu Val Tyr Leu Gly Lys Glu Lys Phe Asp Ser Val His Ser
65 70 75 80

Lys Tyr Met Gly Arg Thr Ser Phe Asp Ser Asp Ser Trp Thr Leu Arg
85 90 95

Leu His Asn Leu Gln Ile Lys Asp Lys Gly Leu Tyr Gln Cys Ile Ile
100 105 110

His His Lys Lys Pro Thr Gly Met Ile Arg Ile His Gln Met Asn Ser
115 120 125

```
Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

<210> SEQ ID NO 23
<211> LENGTH: 435
<212> TYPE: DNA
<213> ORGANISM: Homo sapiens

<400> SEQUENCE: 23

```
atgtggctgc agagcctgct gctcttgggc actgtggcct gcagcatctc tgcacccgcc     60

cgctcgccca gccccagcac gcagccctgg gagcatgtga atgccatcca ggaggcccgg    120

cgtctcctga acctgagtag agacactgct gctgagatga atgaaacagt agaagtcatc    180

tcagaaatgt ttgacctcca ggagccgacc tgcctacaga cccgcctgga gctgtacaag    240

cagggcctgc ggggcagcct caccaagctc aagggcccct tgaccatgat ggccagccac    300

tacaagcagc actgccctcc aaccccggaa acttcctgtg caacccagat tatcaccttt    360

gaaagtttca aagagaacct gaaggacttt ctgcttgtca tcccctttga ctgctgggag    420

ccagtccagg agtga                                                     435
```

<210> SEQ ID NO 24
<211> LENGTH: 144
<212> TYPE: PRT
<213> ORGANISM: Homo sapiens

<400> SEQUENCE: 24

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45
```

-continued

```
Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```